United States Patent
Yang et al.

(10) Patent No.: US 11,478,477 B2
(45) Date of Patent: Oct. 25, 2022

(54) METHOD FOR TREATING CANCER BY COMBINATION OF FAK/ALK/ROS1 INHIBITOR AND EGFR INHIBITOR

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Douglas Dong Fang, Suzhou (CN); Guangfeng Wang, Suzhou (CN)

(73) Assignee: ASCENTAGE PHARMA (SUZHOU) CO., LTD., Jiangsu (CN)

( * ) Notice: Subject to any disclaimer, the term of this patent is extended or adjusted under 35 U.S.C. 154(b) by 0 days.

(21) Appl. No.: 16/627,046

(22) PCT Filed: Jul. 22, 2019

(86) PCT No.: PCT/CN2019/097019
§ 371 (c)(1),
(2) Date: Dec. 27, 2019

(87) PCT Pub. No.: WO2020/024825
PCT Pub. Date: Feb. 6, 2020

(65) Prior Publication Data
US 2021/0330669 A1 Oct. 28, 2021

(30) Foreign Application Priority Data
Jul. 31, 2018 (CN) .......................... 201810859424.1

(51) Int. Cl.
*A61K 31/505* (2006.01)
*A61P 35/00* (2006.01)
*A61K 31/506* (2006.01)
*A61K 31/517* (2006.01)
*A61K 31/519* (2006.01)
*A61K 45/06* (2006.01)

(52) U.S. Cl.
CPC .......... *A61K 31/506* (2013.01); *A61K 31/517* (2013.01); *A61K 31/519* (2013.01); *A61K 45/06* (2013.01); *A61P 35/00* (2018.01)

(58) Field of Classification Search
CPC .............................. A61K 31/505; A61P 35/00
USPC ......................................................... 514/275
See application file for complete search history.

(56) References Cited

FOREIGN PATENT DOCUMENTS

| WO | WO 2015/081813 A1 | 6/2015 |
| WO | WO 2015/130014 A1 | 9/2015 |
| WO | WO 2016/059600 A1 | 4/2016 |
| WO | WO 2017/203532 A1 | 11/2017 |
| WO | WO 2018/044767 A2 | 3/2018 |

OTHER PUBLICATIONS

Jang; J. et al., "Discovery of a potent dual ALK and EGFR T790M inhibitor," European Journal of Medicinal Chemistry 136:497-510 Elsevier Masson SAS, France (2017).
York; E.R. et al., "Tolerable and effective combination of full-dose crizotinib and osimertinib targeting MET amplification sequentially emerging after T790M positivity in EGFR-mutant non-small cell lung cancer," J of Thoracic Oncology 12(7):e85-e88, Elsevier Inc., Netherlands (2017).
International Search Report and Written Opinion in International Application No. PCT/CN2019/097019, National Intellectual Property Administration, China, dated Oct. 22, 2019.
Caira; M.R. et al., "Preparation and crystal characterization of a polymorph, a monohydrate, and an ethyl acetate solvate of the antifungal fluconazole," J Pharm Sci 93(3):601-11, Wiley-Liss, Inc., Hoboken, NJ, and the American Pharmacists Association, Washington, DC, (2004).
Van Tonder; E. et al., "Preparation and physicochemical characterization of 5 niclosamide solvates and 1 hemisolvate," AAPS PharmSciTech 5(1):Article 12, Springer Verlag, Germany (2004).
Bingham, A.L. et al., "Over one hundred solvates of sulfathiazole," Chem. Commun. 603-604, Royal Society of Chemistry, England (2001).
Golubovskaya et al., "Dual Inhibition of Focal Adhesion Kinase and Epidermal Growth Factor Receptor Pathways Cooperatively Induces Death Receptor-mediated Apoptosis in Human Breast Cancer Cells," *J. Bio. Chem* 277:38978-38987, The American Society for Biochemistry and Molecular Biology, Inc. (2002).
Howe et al., "Focal Adhesion Kinase Inhibitors in Combination with Erlotinib Demonstrate Enhanced Anti-Tumor Activity in Non-Small Cell Lung Cancer," *PLoS One* 11(3): e0150567, doi.org/10.1371/journal.pone.0150567 (2016).

*Primary Examiner* — Raymond J Henley, III
(74) *Attorney, Agent, or Firm* — Sterne, Kessler, Goldstein & Fox P.L.L.C.

(57) ABSTRACT

The present invention pertains to the biomedical field, and particularly relates to a method for treating or suppressing a cancer, reducing its severity, lowering its risk or inhibiting its metastasis in an individual. The method comprises administering to the individual a therapeutically effective amount of one or more of a FAK inhibitor, an ALK inhibitor and a ROS1 inhibitor, and a therapeutically effective amount of an EGFR inhibitor. The invention also relates to a pharmaceutical composition or kit comprising one or more of a FAK inhibitor, an ALK inhibitor and a ROS1 inhibitor, and an EGFR inhibitor.

18 Claims, 6 Drawing Sheets

METHOD FOR TREATING CANCER BY COMBINATION OF FAK/ALK/ROS1 INHIBITOR AND EGFR INHIBITOR

TECHNICAL FIELD

The present invention pertains to the biomedical field, and particularly relates to a method for treating or suppressing a cancer, reducing its severity, lowering its risk or inhibiting its metastasis in an individual. The method comprises administering to the individual a therapeutically effective amount of one or more of a FAK inhibitor, an ALK inhibitor and a ROS1 inhibitor, and a therapeutically effective amount of an EGFR inhibitor. The invention also relates to a pharmaceutical composition or kit comprising one or more of a FAK inhibitor, an ALK inhibitor and a ROS1 inhibitor, and an EGFR inhibitor.

BACKGROUND ART

Lung cancer is one of the most common malignant tumors in the world, and it is the cancer with the highest incidence and mortality in China. In the past thirty years, the growth rate of lung cancer in China has reached as high as 465%, and the mortality rate is close to the incidence rate, accounting for about 40% of the global total. Non-small cell lung cancer (NSCLC) accounts for about 80%-85% of lung cancers. Compared with small cell lung cancer, non-small cell lung cancer has a lower degree of deterioration and a relatively late metastasis, but most patients (~75%) have been already in the middle and advanced stage when confirmed, the recurrence rate was high, and the 5-year survival rate was less than 54%.

EGFR mutations, ALK rearrangements, and ROS1 mutations are the most common driver genes in NSCLC. The mutation probabilities of ALK and ROS1 are approximately 5-7%. the EGFR mutations are associated with 30% of NSCLC, and as high as 60% in Asians. A variety of molecularly targeted drugs for the mutations have been used clinically. The targeted drugs currently marketed for EGFR mutations include: icotinib, gefitinib and erlotinib of first generation for 19, 21 exon mutations; afatinib of second generation for 8, 20 exon mutations; and osimertinib (also referred as AZD9291 herein) of third generation for T790M mutation. The targeted drugs for ALK mutations include: crizotinib as first-generation of targeted drug, ceritinib, alectinib and brigatinib as second-generation of targeted drugs, lorlatinib as third-generation of targeted drug, and the like. However, the targeted drugs usually exhibit resistance about 1 year after administration. Thus, overcoming the drug resistance of the targeted drugs or delaying the drug resistance is one of the main objectives in drug research and development.

SUMMARY OF THE INVENTION

In one aspect, the invention provides a method for treating or suppressing a cancer, reducing its severity, lowering its risk or inhibiting its metastasis in an individual, said method comprising administering to the individual a therapeutically effective amount of one or more of a FAK inhibitor, an ALK inhibitor and a ROS1 inhibitor, and a therapeutically effective amount of an EGFR inhibitor.

In another aspect, the invention provides a use of one or more of a FAK inhibitor, an ALK inhibitor and a ROS1 inhibitor in manufacture of a medicament in combination with an EGFR inhibitor for treating or suppressing a cancer, reducing its severity, lowering its risk or inhibiting its metastasis in an individual.

In another aspect, the invention provides one or more of a FAK inhibitor, an ALK inhibitor and a ROS1 inhibitor which is used in combination with an EGFR inhibitor for treating or suppressing a cancer, reducing its severity, lowering its risk or inhibiting its metastasis in an individual.

In another aspect, the invention provides a pharmaceutical composition comprising one or more of a FAK inhibitor, an ALK inhibitor and a ROS1 inhibitor, and an EGFR inhibitor, as well as a pharmaceutically acceptable carrier.

In another aspect, the invention provides a kit, comprising:
 (a) a first component in a first container, the first component comprising one or more of a FAK inhibitor, an ALK inhibitor and a ROS1 inhibitor, and optionally a pharmaceutically acceptable carrier;
 (b) a second component in a second container, the second component comprising an EGFR inhibitor and optionally a pharmaceutically acceptable carrier; and
 (c) an optional specification.

DETAILED DESCRIPTION OF THE INVENTION

Figure 1:
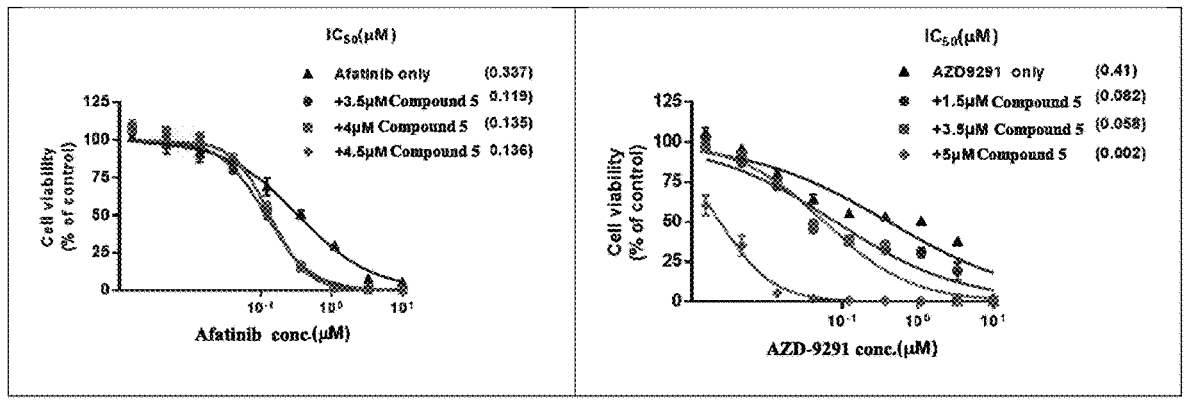
FIG. 1 shows that a combination of Compound 5 with an EGFR inhibitor enhances inhibition effect on the proliferation of NCI-H1975 tumor cells.

Unless otherwise defined below, all technical and scientific terms used herein have the same meanings as commonly understood by one of ordinary skill in the art. References to techniques used herein are intended to refer to techniques that are generally understood in the art, including those obvious changes or equivalent replacements of the techniques for those skilled in the art. While it is believed that the following terms are well understood by those skilled in the art, the following definitions are set forth to better explain the invention.

As used herein, the terms "including", "comprising", "having", "containing" or "comprising", and other variants thereof, are inclusive or open, and do not exclude other unlisted elements or method steps.

As used herein, "FAK" refers to focal adhesion kinase, and "FAK inhibitor" refers to an agent having an inhibitory effect on FAK. In some embodiments, the FAK inhibitor also has an inhibitory effect on one or more other targets (e.g., ALK and/or ROS1).

As used herein, "ALK" refers to anaplasticlymphoma kinase, and "ALK inhibitor" refers to an agent having an inhibitory effect on ALK. In some embodiments, the ALK inhibitor also has an inhibitory effect on one or more other targets (e.g., FAK and/or ROS1).

As used herein, "ROS1" is a tyrosine protein kinase encoded by ROS1 proto-oncogene in human, and "ROS1 inhibitor" refers to an agent having an inhibitory effect on ROS1. In some embodiments, the ROS1 inhibitor also has an inhibitory effect on one or more other targets (e.g., FAK and/or ALK).

As used herein, "EGFR inhibitor" refers to an agent that selectively and efficiently inhibits an epidermal growth factor receptor (EGFR) that carries a certain mutation form.

The term "alkyl" as used herein, alone or as part of another group, refers to an unsubstituted straight or branched aliphatic hydrocarbon containing from 1 to 12 carbon atoms (ie, $C_{1-12}$ alkyl) or an indicated number of carbon atoms, for example, $C_1$ alkyl such as methyl, $C_2$ alkyl such as ethyl, $C_3$ alkyl such as n-propyl or isopropyl, $C_{1-3}$ alkyl such as methyl, ethyl, n-propyl or isopropyl, or the like. In one embodiment, the alkyl is $C_{1-4}$ alkyl. Non-limiting examples of $C_{1-12}$ alkyl include methyl, ethyl, n-propyl, isopropyl, n-butyl, sec-butyl, tert-butyl, isobutyl, 3-pentyl, hexyl, heptyl, octyl, nonyl and decyl. Examples of $C_{1-4}$ alkyl include methyl, ethyl, n-propyl, isopropyl, n-butyl, sec-butyl, tert-butyl, and isobutyl.

The term "cycloalkyl" as used herein, alone or as part of another group, refers to a saturated or partially unsaturated (containing one or two double bonds) cyclic aliphatic hydrocarbon, which comprises 1 or 2 rings having 3 to 12 carbon atoms or an indicated number of carbon atoms (i.e., $C_{3-12}$ cycloalkyl). In one embodiment, the cycloalkyl has two rings. In one embodiment, the cycloalkyl has one ring. In another embodiment, the cycloalkyl group is selected from the group consisting of $C_{3-8}$ cycloalkyl groups. In another embodiment, the cycloalkyl group is selected from the group consisting of $C_{3-6}$ cycloalkyl groups. Non-limiting examples of cycloalkyl include cyclopropyl, cyclobutyl, cyclopentyl, cyclohexyl, cycloheptyl, cyclooctyl, norbornyl, decahydronaphthyl, adamantyl, cyclohexenyl, and cyclopentenyl.

The term "heterocycle" or "heterocyclyl" as used herein, alone or as part of another group, refers to a saturated or partially unsaturated (e.g., comprising one or two double bonds) cyclic group, which comprises 1, 2 or 3 rings having 3 to 14 ring members (i.e., 3- to 14-membered heterocyclyl), wherein at least one carbon atom of one of the rings is replaced by a heteroatom. Each heteroatom is independently selected from the group consisting of atoms of oxygen, sulfur (including sulfoxide and sulfone) and/or nitrogen (which may be oxidized or quaternized). The term "heterocyclyl" is intended to include a group wherein —CH$_2$— in the ring is replaced by —C(=O)—, for example, cyclic ureido (such as 2-imidazolidinone) and cyclic amido (such as β-lactam, γ-lactam, δ-lactam, ε-lactam) and piperazin-2-one. In one embodiment, the heterocyclyl is a 3- to 8-membered cyclic group comprising 1 ring and 1 or 2 oxygen and/or nitrogen atoms. In one embodiment, the heterocyclyl is a 4-, 5- or 6-membered cyclic group comprising 1 ring and 1 or 2 oxygen and/or nitrogen atoms. In one embodiment, the heterocyclyl is a 4- or 6-membered cyclic group comprising 1 ring and 1 or 2 oxygen and/or nitrogen atoms. The heterocyclyl can be attached to the remainder of molecule via any available carbon or nitrogen atom. Non-limiting examples of the heterocyclyl include dioxanyl, tetrahydropyranyl, 2-oxopyrrolidin-3-yl, piperazin-2-one, piperazin-2,6-dione, 2-imidazolidinone, piperidinyl, morpholinyl, piperazinyl, pyrrolidinyl and dihydroindolyl.

As used herein, the term "enantiomeric excess" or "ee" refers to a measure of how much one enantiomer is present relative to another enantiomer. For a mixture of R and S enantiomers, the enantiomeric excess in form of percentage is defined as |R−S|*100, wherein R and S respectively represents mole or weight parts thereof in the mixture, and R+S=1. After knowing the optical rotation of chiral substance, the enantiomeric excess in form of percentage is defined as ($[\alpha]_{obs}/[\alpha]_{max}$)*100, wherein $[\alpha]_{obs}$ represents the optical rotation of the mixture of enantiomers, $[\alpha]_{max}$ represents the optical rotation of pure enantiomer. Enantiomeric excess can be determined using a variety of analytical techniques, including NMR spectroscopy, chiral column chromatography, or optical rotation. The compound of the present invention may have an ee of about 70% or more, such as about 80% or more, 90% or more, 91% or more, 92% or more, 93% or more, 94% or more, 95% or more, 96% or more, 97% or more, 98% or more, or 99% or more.

The term "pharmaceutically acceptable salt", as used herein, includes both acid addition salts and base addition salts of a compound.

Suitable acid addition salts are formed from acids which form non-toxic salts. Examples include acetate, adipate, aspartate, benzoate, besylate, bicarbonate/carbonate, bisulfate/sulfate, borate, camphorsulfonate, citrate, cyclohexylaminosulfonate, ethanedisulfonate, ethanesulfonate, formate, fumarate, glucoheptonate, gluconate, glucuronate, hexafluorophosphate, hibenzate, hydrochloride/chloride, hydrobromide/bromide, hydroiodide/iodide, isethionate, lactate, malate, maleate, malonate, methanesulfonate, methyl sulfate, naphthylate, 2-naphthalenesulfonate, nicotinate, nitrate, orotate, oxalate, palmitate, pamoate, phosphate/hydrogen phosphate/dihydrogen phosphate, pyroglutamate, aldarate, stearate, succinate, tannate, tartrate, tosylate, trifluoroacetate and xinofoate.

Suitable base addition salts are formed from bases which form non-toxic salts. Examples include aluminum salts, arginine salts, benzathine benzylpenicillin salts, calcium salts, choline salts, diethylamine salts, diethanolamine salts, glycine salts, lysine salts, magnesium salts, meglumine salts, ethanolamine salts, potassium salts, sodium salts, tromethamine salts and zinc salts.

For a review of suitable salts, see "Handbook of Pharmaceutical Salts: Properties, Selection, and Use" by Stahl and Wermuth (Wiley-VCH, 2002). Methods for preparing the pharmaceutically acceptable salts of the compounds of the invention are known to those skilled in the art.

The term "solvate" as used herein is a substance formed by combination, physical binding and/or solvation of a compound of the invention with a solvent molecule, such as a disolvate, a monosolvate or a hemisolvate, wherein the ratio of the solvent molecule to the compound of the invention is about 2:1, about 1:1 or about 1:2, respectively. This kind of physical bonding involves ionization and covalent bonding (including hydrogen bonding) in different degrees. In some cases (e.g., when one or more solvent molecules are incorporated into crystal lattice of crystalline solid), the solvate can be isolated. Thus, the solvate comprises both solution phase and isolatable solvates. The compounds of the invention may be in solvated forms with pharmaceutically acceptable solvents (such as water, methanol and ethanol), and the present application is intended to encompass both solvated and unsolvated forms of the compounds of the invention.

One type of solvate is a hydrate. "Hydrate" relates to a specific subset of solvates wherein the solvent molecule is water. Solvates generally function in the form of pharmacological equivalents. The preparation of solvates is known in the art, see for example, M. Caira et al, *J. Pharmaceut. Sci.*, 93(3): 601-611 (2004), which describes the preparation of a solvate of fluconazole with ethyl acetate and water. Similar methods for the preparation of solvates, hemisolvates, hydrates and the like are described by van Tonder et al, *AAPS Pharm. Sci. Tech.*, 5(1): Article 12 (2004) and A.L. Bingham et al, *Chem. Commun.* 603-604 (2001). A representative and non-limiting method for the preparation of solvate involves dissolving a compound of the invention in a desired solvent (organic solvent, water or a mixture thereof) at a temperature above 20° C. to about 25° C., and then the solution is cooled at a rate sufficient to form a crystal, and the crystal is separated by a known method such as filtration. Analytical techniques such as infrared spectroscopy can be used to confirm the presence of the solvent in the crystal of the solvate.

"Pharmaceutically acceptable carrier" in the context of the present invention refers to a diluent, adjuvant, excipient or vehicle together with which the therapeutic agent is administered, and which is suitable for contacting a tissue of human and/or other animals within the scope of reasonable medical judgment, and without excessive toxicity, irritation, allergic reactions, or other problems or complications corresponding to a reasonable benefit/risk ratio.

The pharmaceutically acceptable carriers that can be used in the pharmaceutical compositions or kits of the invention include, but are not limited to, sterile liquids such as water and oils, including those oils derived from petroleum, animals, vegetables or synthetic origins, for example, peanut oil, soybean oil, mineral oil, sesame oil, etc. Water is an exemplary carrier when the pharmaceutical composition is administered intravenously. It is also possible to use physiological saline and an aqueous solution of glucose and glycerin as a liquid carrier, particularly for injection. Suitable pharmaceutical excipients include starch, glucose, lactose, sucrose, gelatin, maltose, chalk, silica gel, sodium stearate, glyceryl monostearate, talc, sodium chloride, skimmed milk powder, glycerin, propylene glycol, water, ethanol and the like. The pharmaceutical composition may further contain a small amount of a wetting agent, an emulsifier or a pH buffering agent as needed. Oral formulations may contain standard carriers such as pharmaceutical grades of mannitol, lactose, starch, magnesium stearate, sodium saccharin, cellulose, magnesium carbonate, and the like. Examples of suitable pharmaceutically acceptable carriers are as described in Remington's Pharmaceutical Sciences (1990).

The pharmaceutical compositions and the components of the kit of the invention may act systemically and/or locally. For this purpose, they may be administered via a suitable route, for example by injection (e.g., intravenous, intraarterial, subcutaneous, intraperitoneal, intramuscular administration, including instillation) or transdermal administration; or by oral, buccal, nasal, transmucosal, topical administration, in form of ophthalmic preparation or by inhalation.

For these routes of administration, the pharmaceutical compositions and the components of the kit of the invention may be administered in a suitable dosage form.

The dosage forms include, but are not limited to, tablets, capsules, troches, hard candy, pulvis, sprays, creams, ointments, suppositories, gels, pastes, lotions, ointments, aqueous suspensions, injectable solutions, elixirs, syrups.

The term "container" as used herein refers to a container for holding a pharmaceutical component. This container can be used for preparation, storage, transportation and/or stand-alone/bulk sale, which is intended to include bottles, cans, vials, flasks, syringes, tubes (e.g., those used in cream products), or any other containers for preparation, containment, storage or distribution of a drug product.

The term "specification/instruction" as used herein refers to an insert, a tag, a label, etc., which records information about a pharmaceutical component located in the container. The information as recorded is typically determined by the regulatory agency (e.g., the United States Food and Drug Administration) that governs the area in which the product is to be sold. Preferably, the package leaflet specifically lists an indication for which the use of the pharmaceutical component is approved. The package leaflet can be made of any material from which information contained therein or thereon can be read. Preferably, the package leaflet is a printable material (e.g., paper, plastic, cardboard, foil, adhesive paper or plastic, etc.) on which the desired information can be formed (e.g., printed or applied).

The term "effective amount" as used herein refers to an amount of active ingredient that, after administration, will relieve to some extent one or more symptoms of the condition being treated.

As used herein, "individual" includes a human or a non-human animal. Exemplary human individual includes a human individual (referred to as a patient) suffering from a disease (such as the disease described herein) or a normal individual. "Non-human animal" in the present invention includes all vertebrates, such as non-mammals (e.g., birds, amphibians, reptiles) and mammals, such as non-human primates, domestic animals, and/or domesticated animals (e.g., sheep, dogs, cats, cows, pigs, etc.).

As used herein, "cancer metastasis" refers to a cancer that spreads (metastasizes) from its original site to another area of the body. Almost all cancers have the potential to metastasize. Whether metastasis will occur depends on complex interactions between multiple tumor cell factors (including type of cancer, degree of maturation (differentiation) of tumor cells, location and age of cancer, and other factors that are not fully understood). There are three ways of metastasis: local expansion from a tumor to a surrounding tissue, arrival through bloodstream to a distant site, or arrival through lymphatic system to an adjacent or distant lymph node. Each cancer can have a representative diffusion route. Tumors are named according to their primary sites (for example, breast cancer that has metastasized to the brain is called metastatic breast cancer that metastasizes to the brain).

As used herein, "resistance" refers to that a cancer cell is resistant to chemotherapy. Cancer cells may acquire resistance to chemotherapy through a range of mechanisms, including mutation or overexpression of drug targets, inactivation of drugs, or elimination of drugs from cells.

Therapeutic Methods and Uses

In one embodiment, the invention provides a method for treating or suppressing a cancer, reducing its severity, lowering its risk or inhibiting its metastasis in an individual, said method comprising administering to the individual a therapeutically effective amount of one or more of a FAK inhibitor, an ALK inhibitor and a ROS1 inhibitor, and a therapeutically effective amount of an EGFR inhibitor.

In another embodiment, the invention provides a use of one or more of a FAK inhibitor, an ALK inhibitor and a ROS1 inhibitor in manufacture of a medicament in combination with an EGFR inhibitor for treating or suppressing a cancer, reducing its severity, lowering its risk or inhibiting its metastasis in an individual.

In another embodiment, the invention provides a use of an EGFR inhibitor in manufacture of a medicament in combination with one or more of a FAK inhibitor, an ALK inhibitor and a ROS1 inhibitor for treating or suppressing a cancer, reducing its severity, lowering its risk or inhibiting its metastasis in an individual.

In another embodiment, the invention provides a use of one or more of a FAK inhibitor, an ALK inhibitor and a ROS1 inhibitor in manufacture of a medicament for treating or suppressing a cancer, reducing its severity, lowering its risk or inhibiting its metastasis in an individual which is being treated with a cancer therapy containing an EGFR inhibitor.

In another embodiment, the invention provides one or more of a FAK inhibitor, an ALK inhibitor and a ROS1 inhibitor which is used in combination with an EGFR inhibitor for treating or suppressing a cancer, reducing its severity, lowering its risk or inhibiting its metastasis in an individual.

In another embodiment, the invention provides an EGFR inhibitor which is used in combination with one or more of a FAK inhibitor, an ALK inhibitor and a ROS1 inhibitor for treating or suppressing a cancer, reducing its severity, lowering its risk or inhibiting its metastasis in an individual.

In another embodiment, the invention provides one or more of a FAK inhibitor, an ALK inhibitor and a ROS1 inhibitor which is used for treating or suppressing a cancer, reducing its severity, lowering its risk or inhibiting its metastasis in an individual which is being treated with a cancer therapy containing an EGFR inhibitor.

In a preferred embodiment, the ALK inhibitor is crizotinib, ceritinib, alectinib, Ensartinib, brigatinib or lorlatinib, or the ALK inhibitor is an ALK inhibitor as described in as in WO 2018/044767 (which is incorporated herein by reference).

In a preferred embodiment, the ALK inhibitor is a compound of Formula I or a pharmaceutically acceptable salt or solvate thereof:

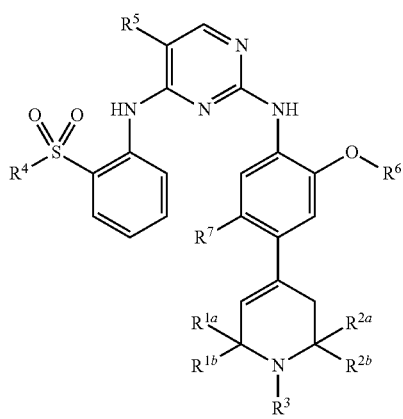

I wherein:

$R^{1a}$ and $R^{1b}$ are independently selected from the group consisting of hydrogen, $C_{1-4}$ alkyl, and $C_{3-6}$ cycloalkyl;

$R^{2a}$ and $R^{2b}$ are independently selected from the group consisting of hydrogen, $C_{1-4}$ alkyl, and $C_{3-6}$ cycloalkyl; and $R^3$ is selected from the group consisting of hydrogen, $C_{1-4}$ alkyl, $C_{3-6}$ cycloalkyl, and 4- to 8-membered heterocyclyl.

In a preferred embodiment, the ALK inhibitor is a compound of Formula III or a pharmaceutically acceptable salt or solvate thereof:

wherein:

$R^{1a}$ and $R^{1b}$ are independently selected from the group consisting of hydrogen, $C_{1-6}$ alkyl, and $C_{3-8}$ cycloalkyl;

$R^{2a}$ and $R^{2b}$ are independently selected from the group consisting of hydrogen, $C_{1-6}$ alkyl, and $C_{3-8}$ cycloalkyl;

$R^3$ is selected from the group consisting of hydrogen, $C_{1-6}$ alkyl, $C_{3-6}$ cycloalkyl, and 4- to 8-membered heterocyclyl, $R^4$ is selected from the group consisting of $C_{1-4}$ alkyl and $C_{3-6}$ cycloalkyl;

$R^5$ is halo;

$R^6$ is selected from the group consisting of $C_{1-4}$ alkyl and $C_{3-6}$ cycloalkyl; and $R^7$ is selected from the group consisting of hydrogen, $C_{1-4}$ alkyl, and $C_{3-6}$ cycloalkyl, with proviso that when $R^{1a}$, $R^{1b}$, $R^{2a}$ and $R^{2b}$ are each hydrogen, then $R^3$ is selected from the group consisting of $C_{3-6}$ cycloalkyl and 4- to 8-membered heterocyclyl.

In a preferred embodiment, the ALK inhibitor is a compound of Formula II or a pharmaceutically acceptable salt or solvate thereof:

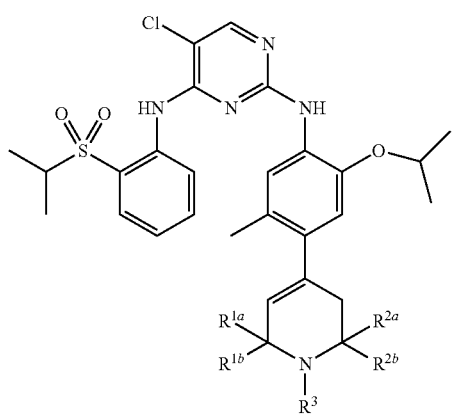

II

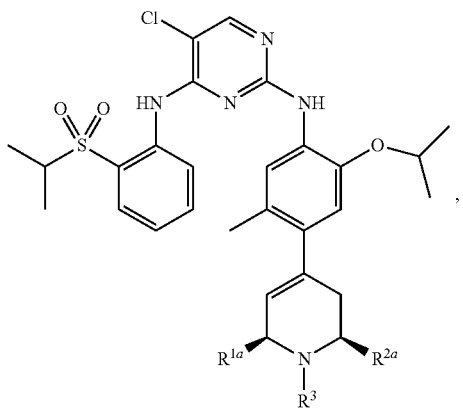

III wherein:

$R^{1a}$ and $R^{2a}$ are each independently selected from the group consisting of $C_{1-4}$ alkyl, and $C_{3-6}$ cycloalkyl; and the compound has an enantiomeric excess of about 90% or more. In some embodiments, the compound has an enantiomeric excess of about 91% or more, about 92% or more, about 93% or more, about 94% or more, about 95% or more, about 96% or more, about 97% or more, about 98% or more, or about 99% or more.

In a preferred embodiment, the ALK inhibitor is a compound of Formula IV or a pharmaceutically acceptable salt or solvate thereof:

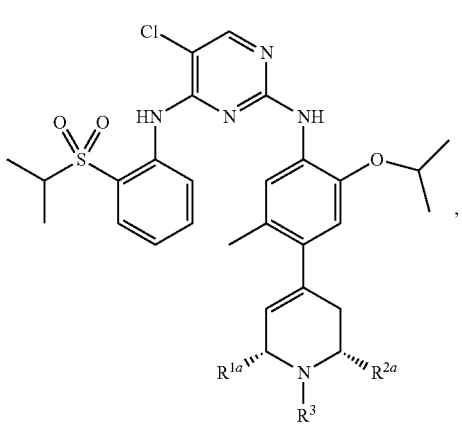

IV wherein:

$R^{1a}$ and $R^{2a}$ are each independently selected from the group consisting of $C_{1-4}$ alkyl, or $C_{3-6}$ cycloalkyl; and the compound has an enantiomeric excess of about 90% or more. In some embodiments, the compound has an enantiomeric excess of about 91% or more, about 92% or more, about 93% or more, about 94% or more, about 95% or more, about 96% or more, about 97% or more, about 98% or more, or about 99% or more.

In a preferred embodiment, the ALK inhibitor is a compound of Formula V or a pharmaceutically acceptable salt or solvate thereof:

V wherein:

$R^{1a}$ and $R^{2a}$ are each independently selected from the group consisting of $C_{1-4}$ alkyl, and $C_{3-6}$ cycloalkyl; and the compound has an enantiomeric excess of about 90% or more. In some embodiments, the compound has an enantiomeric excess of about 91% or more, about 92% or more, about 93% or more, about 94% or more, about 95% or more, about 96% or more, about 97% or more, about 98% or more, or about 99% or more.

In a preferred embodiment, the ALK inhibitor is a compound of Formula VI or a pharmaceutically acceptable salt or solvate thereof:

VI wherein:

$R^{1a}$ and $R^{2a}$ are each independently selected from the group consisting of $C_{1-4}$ alkyl, and $C_{3-6}$ cycloalkyl; and the compound has an enantiomeric excess of about 90% or more. In some embodiments, the compound has an enantiomeric excess of about 91% or more, about 92% or more, about 93% or more, about 94% or more, about 95% or more, about 96% or more, about 97% or more, about 98% or more, or about 99% or more.

In a preferred embodiment, the ALK inhibitor is:

| No. | Structure | Name |
|---|---|---|
| 1 | 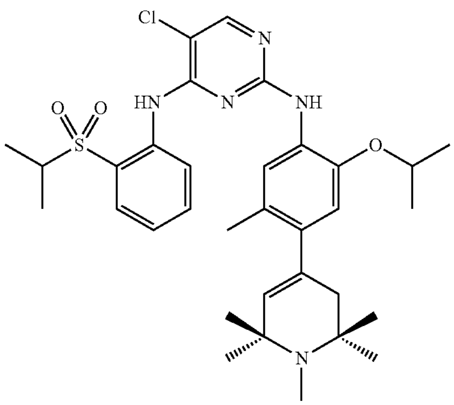 | 5-chloro-$N^2$-(2-isopropoxy-5-methyl-4-(1,2,2,6,6-pentamethyl-1,2,3,6-tetrahydropyridin-4-yl)phenyl)-$N^4$-(2-(isopropylsulfonyl)phenyl)pyrimidine-2,4-diamine; |
| 2 | 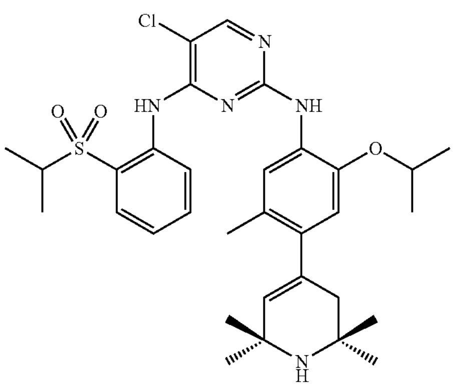 | 5-chloro-$N^2$-(2-isopropoxy-5-methyl-4-(2,2,6,6-tetramethyl-1,2,3,6-tetrahydropyridin-4-yl)phenyl)-$N^4$-(2-(isopropylsulfonyl)phenyl)pyrimidine-2,4-diamine; |
| 3 | 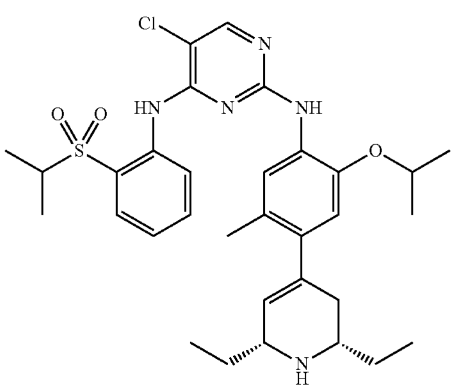 [SMILES: CC[C@H]1CC(c2cc(OC(C)C)c(Nc3ncc(Cl)c(Nc4ccccc4S(=O)(=O)C(C)C)n3)cc2C)=C[C@@H](CC)N1] | 5-chloro-$N^2$-(4-((cis)-2,6-diethyl-1,2,3,6-tetrahydropyridin-4-yl)-2-isopropoxy-5-methylphenyl)-$N^4$-(2-isopropylsulfonyl)phenyl)pyrimidine-2,4-diamine; |
| 4 | 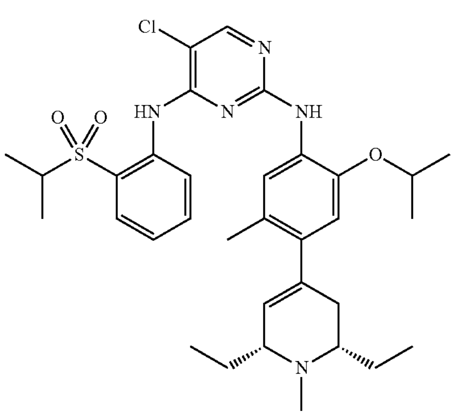 [SMILES: CC[C@H]1CC(c2cc(OC(C)C)c(Nc3ncc(Cl)c(Nc4ccccc4S(=O)(=O)C(C)C)n3)cc2C)=C[C@@H](CC)N1C] | 5-chloro-$N^2$-(4-((cis)-2,6-diethyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |

| No. | Structure | Name |
| --- | --- | --- |
| 5 | 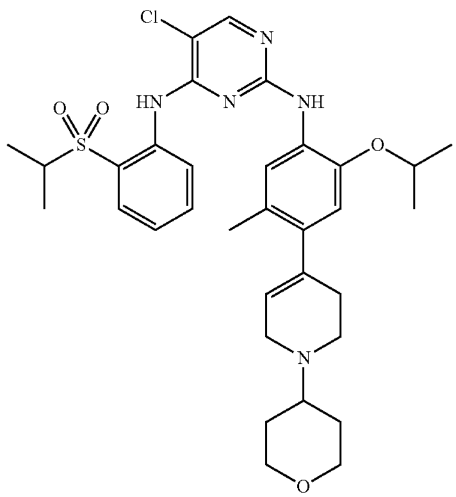 [SMILES: Cc1cc(Nc2ncc(Cl)c(Nc3ccccc3S(=O)(=O)C(C)C)n2)c(OC(C)C)cc1C1=CCN(C2CCOCC2)CC1] | 5-chloro-$N^2$-(2-isopropoxy-5-methyl-4-(1-(tetrahydro-2H-pyran-4-yl)-1,2,3,6-tetrahydropyridin-4-yl)phenyl)-$N^4$-(2-(isopropylsulfonyl)phenyl)pyrimidine-2,4-diamine; |
| 6 | 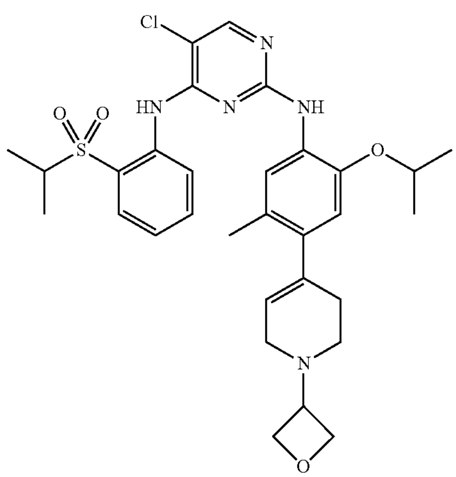 [SMILES: Cc1cc(Nc2ncc(Cl)c(Nc3ccccc3S(=O)(=O)C(C)C)n2)c(OC(C)C)cc1C1=CCN(C2COC2)CC1] | 5-chloro-$N^2$-(2-isopropoxy-5-methyl-4-(1-(oxetan-3-yl)-1,2,3,6-tetrahydropyridin-4-yl)phenyl)-$N^4$-(2-(isopropylsulfonyl)phenyl)pyrimidine-2,4-diamine; |
| 7 | 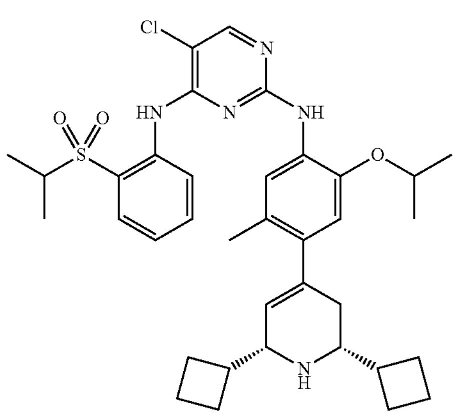 [SMILES: Cc1cc(Nc2ncc(Cl)c(Nc3ccccc3S(=O)(=O)C(C)C)n2)c(OC(C)C)cc1C1=C[C@@H](C2CCC2)N[C@@H](C2CCC2)C1] | 5-chloro-$N^2$-(4-((cis)-2,6-dicyclobutyl-1,2,3,6-tetrahydropyridin-4-yl)-2-isopropoxy-5-methylphenyl)-$N^4$-(2-(isopropylsulfonyl)phenyl)pyrimidine-2,4-diamine; |

-continued

| No. | Structure | Name |
|---|---|---|
| 8 | 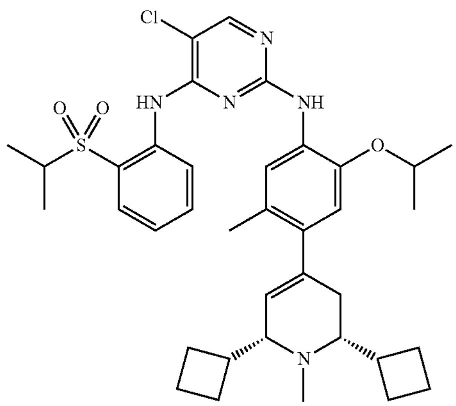 [SMILES: Cc1cc(Nc2ncc(Cl)c(Nc3ccccc3S(=O)(=O)C(C)C)n2)c(OC(C)C)cc1C1=C[C@@H](C2CCC2)N(C)[C@@H](C2CCC2)C1] | 5-chloro-$N^2$-(4-((cis)-2,6-dicyclobutyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 9 | 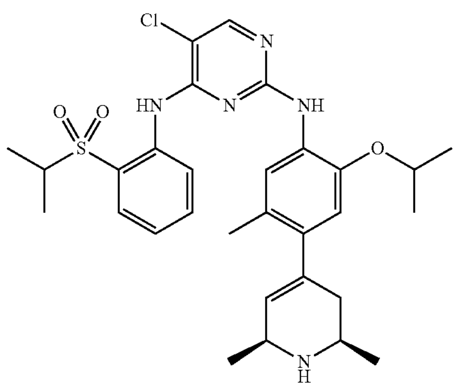 [SMILES: Cc1cc(Nc2ncc(Cl)c(Nc3ccccc3S(=O)(=O)C(C)C)n2)c(OC(C)C)cc1C1=C[C@H](C)N[C@H](C)C1] | 5-chloro-$N^2$-(4-((cis)-2,6-dimethyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 10 | 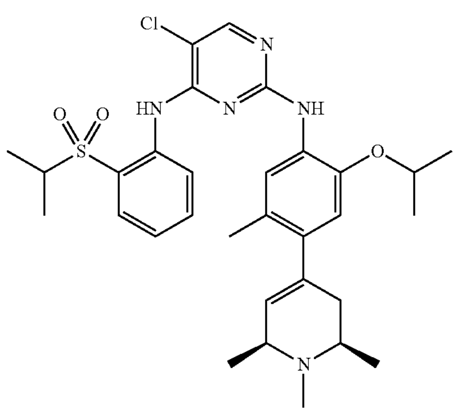 [SMILES: Cc1cc(Nc2ncc(Cl)c(Nc3ccccc3S(=O)(=O)C(C)C)n2)c(OC(C)C)cc1C1=C[C@H](C)N(C)[C@H](C)C1] | 5-chloro-$N^2$-(2-isopropoxy-5-methyl-4-((cis)-1,2,6-trimethyl-1,2,3,6-tetrahydropyridin-4-yl)phenyl)-$N^4$-(2-(isopropylsulfonyl)phenyl)pyrimidine-2,4-diamine; |
| 11 | 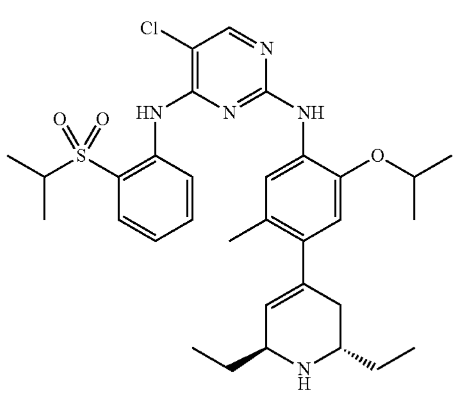 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1] | 5-chloro-$N^2$-(4-((trans)-2,6-diethyl-1,2,3,6-tetrahydropyridin-4-yl)-2-isopropoxy-5-methylphenyl)-$N^4$-(2-(isopropylsulfonyl)phenyl)pyrimidine-2,4-diamine; |

-continued

| No. | Structure | Name |
|---|---|---|
| 12 | 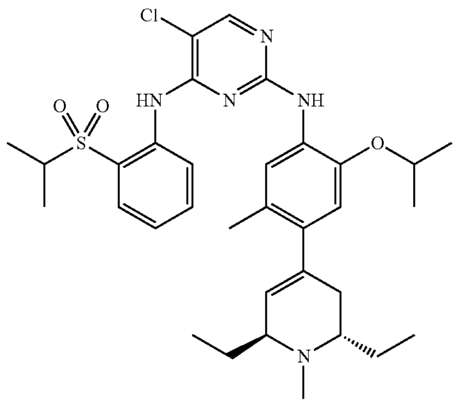 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C] | 5-chloro-$N^2$-(4-((trans)-2,6-diethyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 13 | 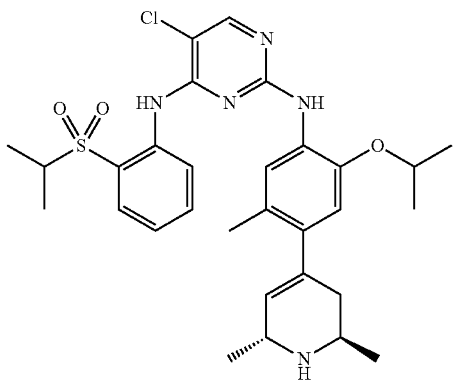 [SMILES: Cc1cc(Nc2ncc(Cl)c(Nc3ccccc3S(=O)(=O)C(C)C)n2)c(OC(C)C)cc1C1=C[C@@H](C)N[C@H](C)C1] | 5-chloro-$N^2$-(4-((trans)-2,6-dimethyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 14 | 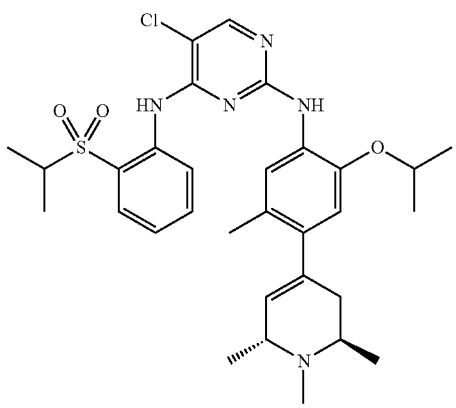 [SMILES: Cc1cc(Nc2ncc(Cl)c(Nc3ccccc3S(=O)(=O)C(C)C)n2)c(OC(C)C)cc1C1=C[C@@H](C)N(C)[C@H](C)C1] | 5-chloro-$N^2$-(2-isopropoxy-5-methyl-4-((trans)-1,2,6-trimethyl-1,2,3,6-tetrahydropyridin-4-yl)phenyl)-$N^4$-(2-(isopropylsulfonyl)phenyl)pyrimidine-2,4-diamine; |
| 15 | 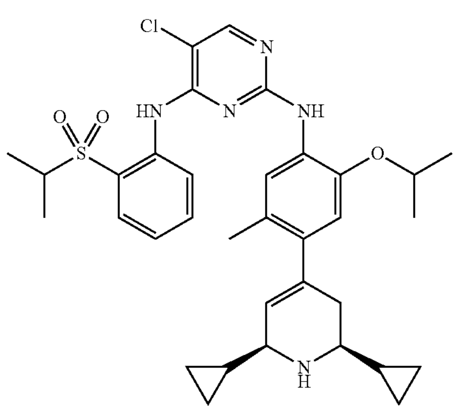 [SMILES: Cc1cc(Nc2ncc(Cl)c(Nc3ccccc3S(=O)(=O)C(C)C)n2)c(OC(C)C)cc1C1=C[C@H](C2CC2)N[C@H](C2CC2)C1] | 5-chloro-$N^2$-(4-((cis)-2,6-dicyclopropyl-1,2,3,6-tetrahydropyridin-4-yl)-2-isopropoxy-5-methylphenyl)-$N^4$-(2-(isopropylsulfonyl)phenyl)pyrimidine-2,4-diamine; |

-continued

| No. | Structure | Name |
|---|---|---|
| 16 | 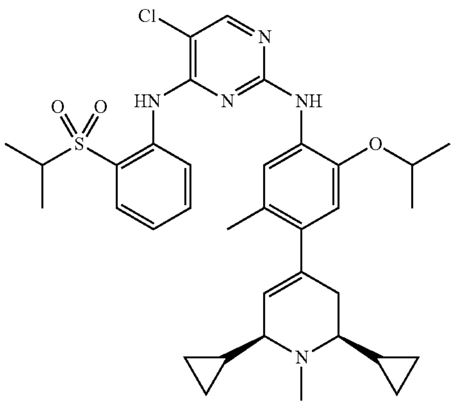 [SMILES: Cc1cc(Nc2ncc(Cl)c(Nc3ccccc3S(=O)(=O)C(C)C)n2)c(OC(C)C)cc1C1=C[C@H](C2CC2)N(C)[C@H](C2CC2)C1] | 5-chloro-$N^2$-(4-((cis)-2,6-dicyclopropyl-1-methyl-1,2,3,6-tetra-hydropyridin-4-yl)-2-isopropoxy-5-methylphenyl)-$N^4$-(2-(isopropylsulfonyl)phenyl)pyrimidine-2,4-diamine; |
| 17 | 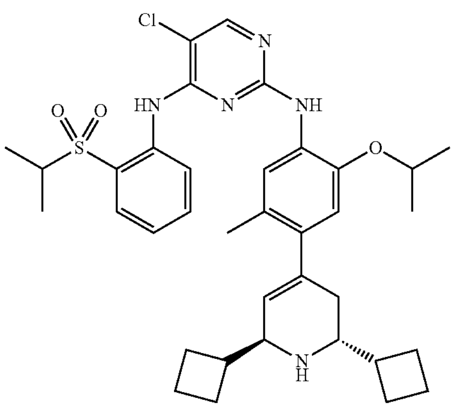 [SMILES: Cc1cc(Nc2ncc(Cl)c(Nc3ccccc3S(=O)(=O)C(C)C)n2)c(OC(C)C)cc1C1=C[C@H](C2CCC2)N[C@@H](C2CCC2)C1] | 5-chloro-$N^2$-(4-((trans)-2,6-dicyclobutyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 18 | 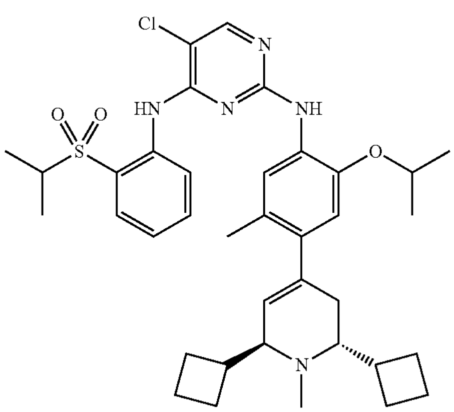 [SMILES: Cc1cc(Nc2ncc(Cl)c(Nc3ccccc3S(=O)(=O)C(C)C)n2)c(OC(C)C)cc1C1=C[C@H](C2CCC2)N(C)[C@@H](C2CCC2)C1] | 5-chloro-$N^2$-(4-((trans)-2,6-dicyclobutyl-1-methyl-1,2,3,6-tetra-hydroypyridin-4-yl)-2-isopropoxy-5-methylphenyl)-$N^4$-(2-(isopropylsulfonyl)phenyl)pyrimidine-2,4-diamine; |
| 19 | 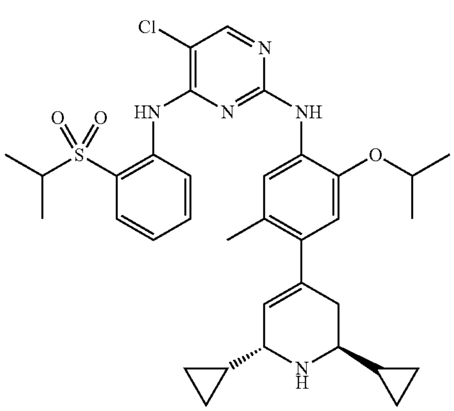 [SMILES: Cc1cc(Nc2ncc(Cl)c(Nc3ccccc3S(=O)(=O)C(C)C)n2)c(OC(C)C)cc1C1=C[C@@H](C2CC2)N[C@H](C2CC2)C1] | 5-chloro-$N^2$-(4-((trans)-2,6-dicyclopropyl-1,2,3,6-tetrahydropyridin-4-yl)-2-isopropoxy-5-methylphenyl)-$N^4$-(2-(isopropylsulfonyl)phenyl)pyrimidine-2,4-diamine; |

-continued

| No. | Structure | Name |
|---|---|---|
| 20 | 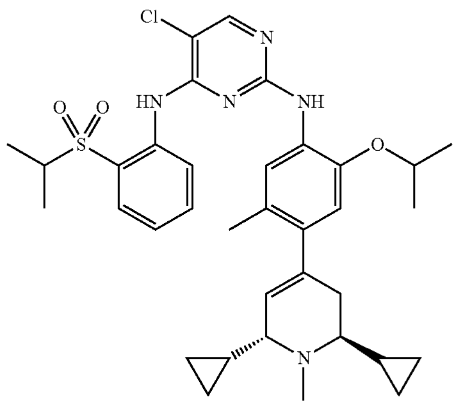 [SMILES: Cc1cc(Nc2ncc(Cl)c(Nc3ccccc3S(=O)(=O)C(C)C)n2)c(OC(C)C)cc1C1=C[C@@H](C2CC2)N(C)[C@H](C2CC2)C1] | 5-chloro-$N^2$-(4-((trans)-2,6-dicyclopropyl-1-methyl-1,2,3,6-tetra-hydroypyridin-4-yl)-2-isopropoxy-5-methylphenyl)-$N^4$-(2-(isopropylsulfonyl)phenyl)pyrimidine-2,4-diamine; |
| 21 | 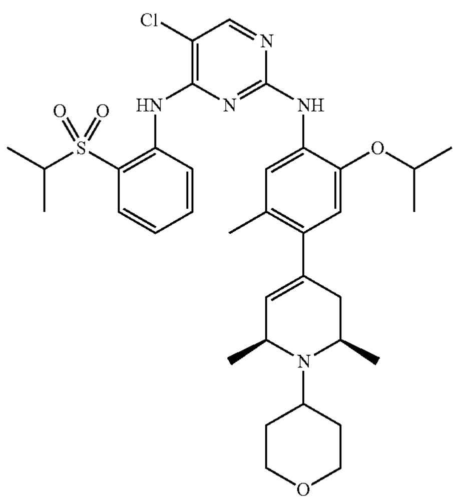 [SMILES: Cc1cc(Nc2ncc(Cl)c(Nc3ccccc3S(=O)(=O)C(C)C)n2)c(OC(C)C)cc1C1=C[C@H](C)N(C2CCOCC2)[C@H](C)C1] | 5-chloro-$N^2$-(4-((cis)-2,6-dimethyl-1-(tetrahydro-2H-pyran-4-yl)-1,2,3,6-tetrahydropyridin-4-yl)-2-isopropoxy-5-methylphenyl)-$N^4$-(2-(isopropylsulfonyl)phenyl)pyrimidine-2,4-diamine; |
| 22 | 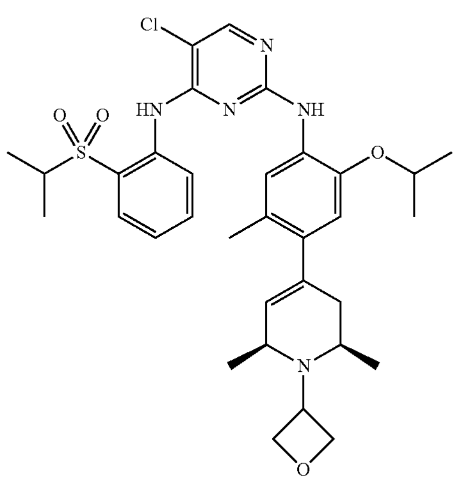 [SMILES: Cc1cc(Nc2ncc(Cl)c(Nc3ccccc3S(=O)(=O)C(C)C)n2)c(OC(C)C)cc1C1=C[C@H](C)N(C2COC2)[C@H](C)C1] | 5-chloro-$N^2$-(4-((cis)-2,6-dimethyl-1-(oxetan-3-yl)-1,2,3,6-tetra-hydropyridin-4-yl)-2-isopropoxy-5-methylphenyl)-$N^4$-(2-(isopropylsulfonyl)phenyl)pyrimidine-2,4-diamine; |

| No. | Structure | Name |
|---|---|---|
| 23 | 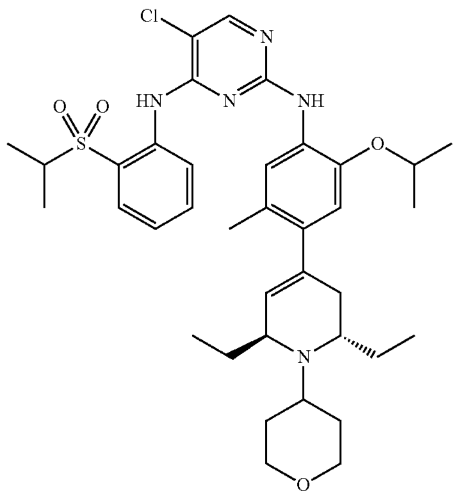 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C1CCOCC1] | 5-chloro-N²-(4-((trans)-2,6-diethyl-1-(tetrahydro-2H-pyran-4-yl-1,2,3,6-tetrahydropyridin-4-yl)-2-isopropoxy-5-methylphenyl)-N⁴-(2-(isopropylsulfonyl)phenyl)pyrimidine-2,4-diamine; |
| 24 | 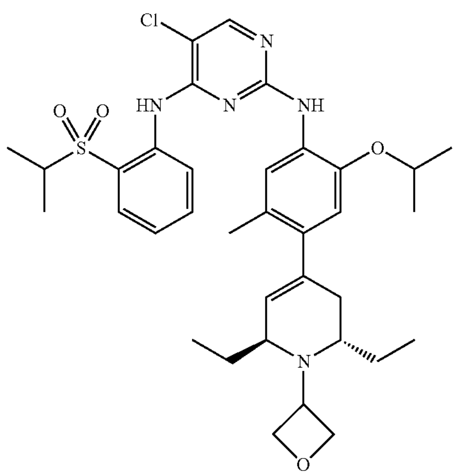 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C1COC1] | 5-chloro-N²-(4-((2S,6S)-2,6-diethyl-1-(oxetan-3-yl)-1,2,3,6-tetrahydropyridin-4-yl)-2-isopropoxy-5-methylphenyl)-N⁴-(2-(isopropylsulfonyl)phenyl)pyrimidine-2,4-diamine; |
| 25 | 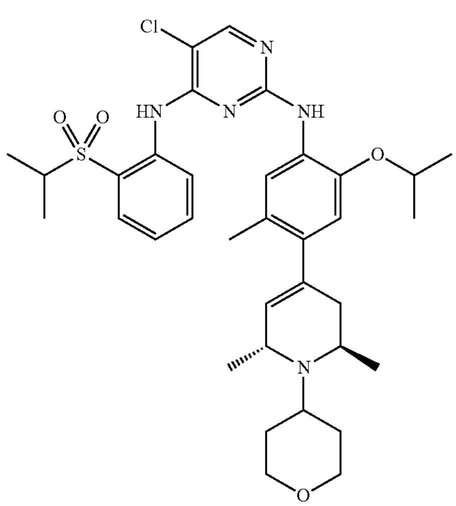 [SMILES: Cc1cc(Nc2ncc(Cl)c(Nc3ccccc3S(=O)(=O)C(C)C)n2)c(OC(C)C)cc1C1=C[C@@H](C)N(C2CCOCC2)[C@H](C)C1] | 5-chloro-N²-(4-((trans)-2,6-dimethyl-1-(tetrahydro-2H-pyran-4-yl)-1,2,3,6-tetrahydropyridin-4-yl)-2-isopropoxy-5-methylphenyl)-N⁴-(2-(isopropylsulfonyl)phenyl)pyrimidine-2,4-diamine; |

| No. | Structure | Name |
|---|---|---|
| 26 | 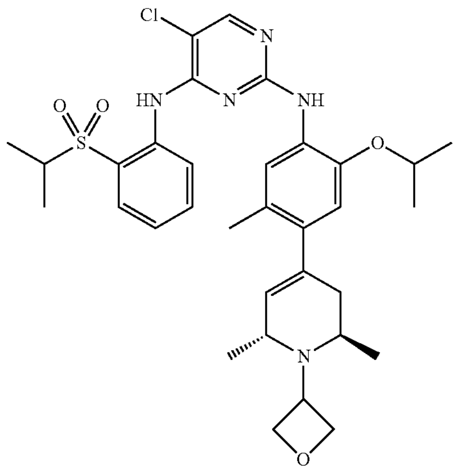 [SMILES: Cc1cc(Nc2ncc(Cl)c(Nc3ccccc3S(=O)(=O)C(C)C)n2)c(OC(C)C)cc1C1=C[C@@H](C)N(C2COC2)[C@H](C)C1] | 5-chloro-N²-(4-((trans)-2,6-dimethyl-1-(oxetan-3-yl)-1,2,3,6-tetrahydropyridin-4-yl)-2-isopropoxy-5-methylphenyl)-N⁴-(2-(isopropylsulfonyl)phenyl)pyrimidine-2,4-diamine; |
| 27 | 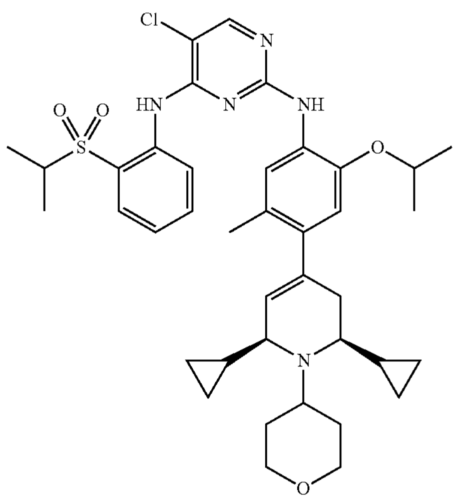 [SMILES: Cc1cc(Nc2ncc(Cl)c(Nc3ccccc3S(=O)(=O)C(C)C)n2)c(OC(C)C)cc1C1=C[C@H](C2CC2)N(C2CCOCC2)[C@H](C2CC2)C1] | 5-chloro-N²-(4-((cis)-2,6-dicyclopropyl-1-(tetrahydro-2H-pyran-4-yl)-1,2,3,6-tetrahydropyridin-4-yl)-2-isopropoxy-5-methylphenyl)-N⁴-(2-(isopropylsulfonyl)phenyl)pyrimidine-2,4-diamine; |
| 28 | 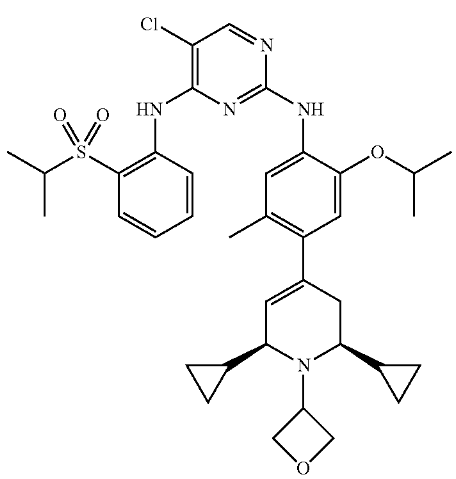 [SMILES: Cc1cc(Nc2ncc(Cl)c(Nc3ccccc3S(=O)(=O)C(C)C)n2)c(OC(C)C)cc1C1=C[C@H](C2CC2)N(C2COC2)[C@H](C2CC2)C1] | 5-chloro-N²-(4-((cis)-2,6-dicyclopropyl-1-(oxetan-3-yl)-1,2,3,6-tetrahydropyridin-4-yl)-2-isopropoxy-5-methylphenyl)-N⁴-(2-(isopropylsulfonyl)phenyl)pyrimidine-2,4-diamine; |

-continued

| No. | Structure | Name |
|---|---|---|
| 29 | 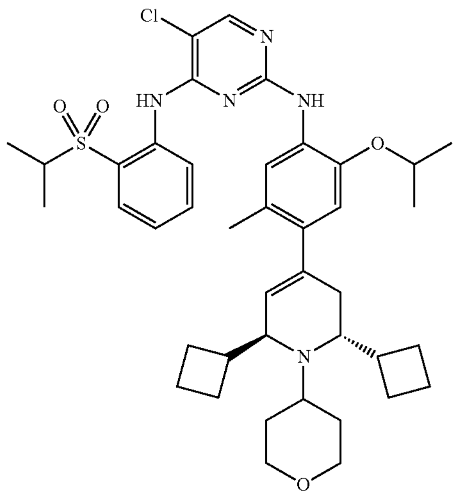 [SMILES: Cc1cc(Nc2ncc(Cl)c(Nc3ccccc3S(=O)(=O)C(C)C)n2)c(OC(C)C)cc1C1=C[C@H](C2CCC2)N(C2CCOCC2)[C@@H](C2CCC2)C1] | 5-chloro-N²-(4-((trans)-2,6-dicyclobutyl-1-(tetrahydro-2H-pyran-4-yl)-1,2,3,6-tetrahydropyridin-4-yl)-2-isopropoxy-5-methylphenyl)-N⁴-(2-(isopropylsulfonyl)phenyl)pyrimidine-2,4-diamine; |
| 30 | 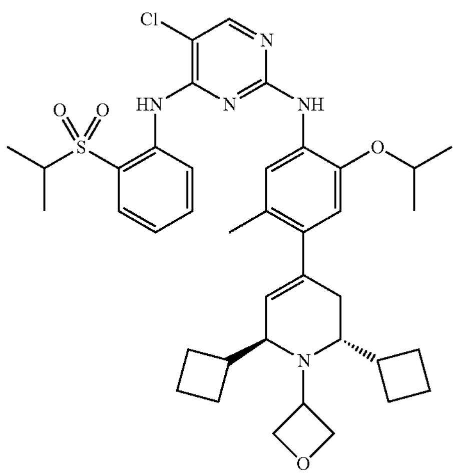 [SMILES: Cc1cc(Nc2ncc(Cl)c(Nc3ccccc3S(=O)(=O)C(C)C)n2)c(OC(C)C)cc1C1=C[C@H](C2CCC2)N(C2COC2)[C@@H](C2CCC2)C1] | 5-chloro-N²-(4-((trans)-2,6-dicyclobutyl-1-(oxetan-3-yl)-1,2,3,6-tetrahydropyridin-4-yl)-2-isopropoxy-5-methylphenyl)-N⁴-(2-(isopropylsulfonyl)phenyl)pyrimidine-2,4-diamine; |
| 31 | 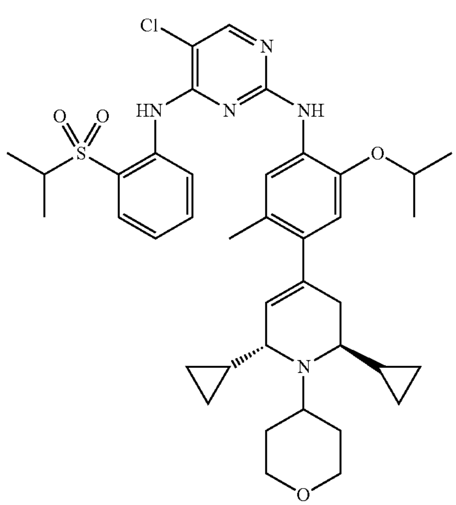 [SMILES: Cc1cc(Nc2ncc(Cl)c(Nc3ccccc3S(=O)(=O)C(C)C)n2)c(OC(C)C)cc1C1=C[C@@H](C2CC2)N(C2CCOCC2)[C@H](C2CC2)C1] | 5-chloro-N²-(4-((trans)-2,6-dicyclopropyl-1-(tetrahydro-2H-pyran-4-yl)-1,2,3,6-tetrahydropyridin-4-yl)-2-isopropoxy-5-methylphenyl)-N⁴-(2-(isopropylsulfonyl)phenyl)pyrimidine-2,4-diamine; or |

| No. | Structure | Name |
|---|---|---|
| 32 | 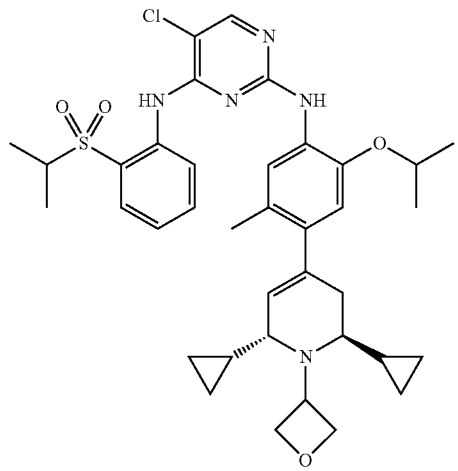 [SMILES: Cc1cc(Nc2ncc(Cl)c(Nc3ccccc3S(=O)(=O)C(C)C)n2)c(OC(C)C)cc1C1=C[C@@H](C2CC2)N(C2COC2)[C@H](C2CC2)C1] | 5-chloro-N²-(4-((trans)-2,6-dicyclopropyl-1-(oxetan-3-yl)-1,2,3,6-tetrahydropyridin-4-yl)-2-isopropoxy-5-methylphenyl)-N⁴-(2-(isopropylsulfonyl)phenyl)pyrimidine-2,4-diamine. |

In a preferred embodiment, the ALK inhibitor is 5-chloro-N²-(2-isopropoxy-5-methyl-4-(1-(tetrahydro-2H-pyran-4-yl)-1,2,3,6-tetrahydropyridin-4-yl)phenyl)-N⁴-(2-(isopropylsulfonyl)phenyl)pyrimidine-2,4-diamine, or a pharmaceutically acceptable salt or hydrate thereof.

In a preferred embodiment, the EGFR inhibitor is selected from the group consisting of icotinib, osimertinib (AZD9291), afatinib, Avitinib, gefitinib, erlotinib, lapatinibxylenesulphonate, neratinib, cetuximab, pamumab, vannameib, nexizumab, AG-490, tyrosine phosphorylation inhibitor AG 1478, CL-387, CL-785, oncogene inhibitor analog, PD 168393, PKC-412, PD 174265, tyrosine phosphorylation inhibitor 51, butein, valanib dihydrochloride, tyrosine phosphorylation inhibitor 47, AG 494, tyrosine phosphorylation inhibitor AG 112, AZD8931, CUDC-101, XL647, AG 43, (+)shy-Aeroplysinin-1, PD 153035, OSI-420 free base (demethyl erlotinib), WZ4002, tyrosine phosphorylation inhibitor B44, (−)enantiomer, tyrosine phosphorylation inhibitor B44, (+)enantiomer, PD161570, neratinib, HDS029, erlotinib-d6, lavendustin C methyl ester, RO 106-9920, tyrosine phosphorylation inhibitor AG 99, AG 555, AG 556, RG-13022, tyrosine phosphorylation inhibitor RG 14620, DAPH, BPIQ-II HCl salt, didesmethyl erlotinib hydrochloride, demethyl erlotinib acetate, PD 153035 hydrochloride, BMX 1382, GW2974, PD 166285, pilitinib, EGFR inhibitor III, AST 1306, gefitinib hydrochloride, ARRY334543, dacomitinib, gefitinib O-methyl-D3, OSI-420-d4, free base (demethyl erlotinib-d4), LFM-A12, BPDQ, tyrosine phosphorylation inhibitor 47, tyrosine phosphorylation inhibitor AG 528, BPIQ-I, gefitinib dihydrochloride, carnitinib dihydrochloride, GW 583340 dihydrochloride, BIBU 1361 dihydrochloride, TAK 285, WZ 3146, WZ8040, O-demethyl gefitinib, O-demorpholinopropyl gefitinib, TAK 165, CGP 74514A.

In a preferred embodiment, the EGFR inhibitor is preferably afatinib, Avitinib or osimertinib (AZD9291).

In a preferred embodiment, the cancer is selected from the group consisting of bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroturbo chargeoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, and hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), chronic myeloid leukemia (CML).

In a more preferred embodiment, the cancer is a solid tumor with high expression of FAK, an ALK/ROS1 positive tumor, a mutant tumor (preferably an EGFR$^{T790M}$ mutant tumor (more preferably a tumor carrying an EGFR$^{T790M}$ mutation), an ALK mutant tumor or a ROS1 mutant tumor), a drug-resistant tumor (preferably an EGFR inhibitor-resistant tumor or an ALK inhibitor-resistant tumor), wherein the tumor is preferably non-small cell lung cancer.

In a preferred embodiment, one or more of the FAK inhibitor, ALK inhibitor and ROS1 inhibitor is administrated in an amount of from about 0.005 mg/day to about 5000 mg/day, such as an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

In a preferred embodiment, one or more of the FAK inhibitor, ALK inhibitor and ROS1 inhibitor is administrated in an amount of from about 1 ng/kg to about 200 mg/kg, about 1 μg/kg to about 100 mg/kg, or about 1 mg/kg to about 50 mg/kg per unit dose, for example, administrated in an amount of about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625

µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg per unit dose, and administrated with one or more (e.g., 1, 2, 3, 4, 5, 6, 7, 8, 9 or 10) unit doses per day.

In a preferred embodiment, the EGFR inhibitor is administrated in an amount of from 0.005 mg/day to about 5000 mg/day, for example, about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

In a preferred embodiment, the EGFR inhibitor is administrated in an amount of from about 1 ng/kg to about 200 mg/kg, from about 1 µg/kg to about 100 mg/kg, or from about 1 mg/kg to about 50 mg/kg per unit dose, for example, administrated in an amount of about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg per unit dose, and administered with one or more (e.g., 1, 2, 3, 4, 5, 6, 7, 8, 9, or 10) unit doses per day.

In a preferred embodiment, one or more of the FAK inhibitor, ALK inhibitor and ROS1 inhibitor and the EGFR inhibitor are administered together, simultaneously, sequentially or alternately.

In a preferred embodiment, one or more of the FAK inhibitor, ALK inhibitor and ROS1 inhibitor and/or the EGFR inhibitor are administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days, or at least 50 days.

In a preferred embodiment, one or more of the FAK inhibitor, ALK inhibitor and ROS1 inhibitor and/or the EGFR inhibitor are administered for one or more (e.g., 1, 2, 3, 4, 5, 6, 7, 8, 9 or 10) courses of treatment, in which each of the courses lasts at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days, or at least 50 days; and there is an interval of 0, 1, 2, 3, 4, 5, 6, 7, 8, 9, 10 days, two weeks, three weeks or four weeks between every two courses of treatment.

In a preferred embodiment, when there are a plurality of courses of treatment, the amount of the FAK inhibitor, ALK inhibitor, ROS1 inhibitor and/or EGFR inhibitor administered in each course of treatment is same or different. In a more preferred embodiment, the amount of the FAK inhibitor, ALK inhibitor, ROS1 inhibitor and/or EGFR inhibitor administered during the previous course of treatment is 1-10 times, preferably 1-5 times, such as 1.5, 2, 2.5, 3, 3.5, 4, 4.5 or 5 times, the amount administered during the subsequent course of treatment.

In a preferred embodiment, one or more of the FAK inhibitor, ALK inhibitor and ROS1 inhibitor as well as the EGFR inhibitor are administrated via the same (e.g., oral) or different routes (e.g., oral and parenteral (e.g., injection), respectively).

In a preferred embodiment, the EGFR inhibitor is administrated in a lower dose in comparison with the dose of EGFR inhibitor that is administered alone or when one or more of the FAK inhibitor, ALK inhibitor, and ROS1 inhibitor is not administered.

In a preferred embodiment, one or more of the FAK inhibitor, ALK inhibitor and ROS1 inhibitor enhances the therapeutic efficacy of EGFR inhibitor in treatment of a cancer and/or reduces a side-effect of EGFR inhibitor in treatment of a cancer.

In a preferred embodiment, the invention provides a use of one or more of a FAK inhibitor, an ALK inhibitor and a ROS1 inhibitor in manufacture of a medicament for enhancing the efficacy of an EGFR inhibitor in treatment of a cancer and/or reducing a side-effect of an EGFR inhibitor in treatment of a cancer.

In a preferred embodiment, the individual suffers from an advanced cancer.

In a preferred embodiment, the individual suffers from a refractory cancer, a recurrent cancer or a drug-resistant cancer, in particular a cancer that is resistant to a cancer therapy comprising an EGFR inhibitor.

In another embodiment, the invention provides a use of one or more of a FAK inhibitor, an ALK inhibitor and a ROS1 inhibitor in manufacture of a medicament in combination with an EGFR inhibitor for treating an individual with a drug-resistant cancer, particularly a cancer resistant to a cancer therapy containing the EGFR inhibitor.

Pharmaceutical Compositions and Kits

In another embodiment, the invention provides a pharmaceutical composition comprising one or more of a FAK inhibitor, an ALK inhibitor and a ROS1 inhibitor, and an EGFR inhibitor, and a pharmaceutically acceptable carrier.

In a preferred embodiment, the pharmaceutical composition comprises an ALK inhibitor (preferably an ALK inhibitor as defined above) and an EGFR inhibitor (preferably an EGFR inhibitor as defined above) and a pharmaceutically acceptable carrier.

In another embodiment, the invention provides a kit comprising:

(a) a first component in a first container, the first component comprising one or more of a FAK inhibitor, an ALK inhibitor (preferably an ALK inhibitor as defined above) and a ROS1 inhibitor, and optionally a pharmaceutically acceptable carrier;

(b) a second component in a second container, the second component comprising an EGFR inhibitor, preferably an EGFR inhibitor as defined above, and optionally a pharmaceutically acceptable carrier; and (c) an optional specification.

EXAMPLE

In order to make the objects and technical solutions of the present invention clearer, the present invention will be further described below in conjunction with specific example. It should be understood that the examples are not intended to limit the scope of the invention. Further, specific experimental methods not mentioned in the following examples were carried out in accordance with a conventional experimental method.

The abbreviations in the context have the following meanings:

| Abbreviation | Meaning |
|---|---|
| CDCl$_3$ | Deuterated chloroform |
| Cs$_2$CO$_3$ | Barium carbonate |
| DME | Ethylene glycol dimethyl ether |
| HCl | Hydrochloric acid |
| H$_2$O | Water |
| HPLC | High performance liquid chromatography |
| K$_2$CO$_3$ | Potassium carbonate |
| NaHCO$_3$ | Sodium bicarbonate |
| Na$_2$SO$_4$ | Sodium sulfate |
| Pd(dppf)Cl$_2$ | [1,1'-bis(diphenylphosphino)ferrocene]palladium dichloride |
| Pd(OAc)$_2$ | Palladium acetate |
| THF | Tetrahydrofuran |
| Xantphos | 4,5-bis(diphenylphosphino)-9,9-dimethylxanthene |

Example 1

Preparation of 5-chloro-N$^2$-(2-isopropoxy-5-methyl-4-(1-(tetrahydro-2H-pyran-4-yl)-1,2,3,6-tetrahydropyridin-4-yl)phenyl)-N$^4$-(2-(isopropylsulfonyl)phenyl)pyrimidine-2,4-diamine Step A: Synthesis of tert-butyl 4-(5-fluoro-2-methyl-4-nitrophenyl)-3,6-dihydropyridine-1(2H)-carboxylate Tert-butyl 4-(4,4,5,5-tetramethyl-1,3,2-dioxaborolan-2-yl)-3,6-dihydropyridine-1(2H)-carboxylate (620 mg, 2 mmol), Pd(dppf)Cl$_2$ (58 mg, 0.08 mmol), and K$_2$CO$_3$ (828 mg, 6 mmol) were added to a solution of 1-bromo-5-fluoro-2-methyl-4-nitrobenzene (470 mg, 2 mmol) in DME-H$_2$O (22 mL, 10:1 mixture). The mixture was stirred at 80° C. for 12 hr under nitrogen. The reaction was cooled to room temperature and the product was extracted with ethyl acetate. Solvent was removed under reduced pressure and the residue was purified by silica gel chromatography with hexane/ethyl acetate (9/1, v/v) to afford the title compound of Step A (640 mg, 95% yield) as a slightly yellow oil.

$^1$H NMR (400 MHz, CDCl$_3$) δ ppm 7.89 (d, J=7.5 Hz, 1H), 7.02 (d, J=11.5 Hz, 1H), 5.68 (s, 1H), 4.10-4.07 (m, 2H), 3.65 (t, J=5.6 Hz, 2H), 2.39-2.32 (m, 2H), 2.33 (s, 3H), 1.52 (s, 9H).

Step B: Synthesis of tert-butyl 4-(5-isopropoxy-2-methyl-4-nitrophenyl)-3,6-dihydropyridine-1(2H)-carboxylate To a solution of tert-butyl 4-(5-fluoro-2-methyl-4-nitrophenyl)-3,6-dihydropyridine-1(2H)-carboxylate (640 mg, 1.9 mmol) in 20 mL of 2-propanol, Cs$_2$CO$_3$ (1.862 g, 5.7 mmol) was added. The mixture was stirred at 60° C. overnight, and after cooling to room temperature, most of the 2-propanol was evaporated under reduced pressure. Water was added, and the solution was extracted with ethyl acetate. The organic layers were combined, dried over anhydrous Na$_2$SO$_4$, concentrated, and the crude product was purified by silica gel chromatography with hexane/ethyl acetate (8/2, v/v) to afford the title compound of Step B (650 mg, 91%) as a yellow oil.

$^1$H NMR (400 MHz, CDCl$_3$) δ 7.63 (s, 1H), 6.79 (s, 1H), 5.62 (s, 1H), 4.65-4.62 (m, 1H), 4.10-4.07 (m, 2H), 3.64 (t, J=5.6 Hz, 2H), 2.36-2.34 (m, 2H), 2.25 (s, 3H), 1.52 (s, 9H), 1.39 (d, J=6.1 Hz, 6H).

Step C: Synthesis of 4-(5-isopropoxy-2-methyl-4-nitrophenyl)-1-(tetrahydro-2H-pyran-4-yl)-1,2,3,6-tetrahydropyridine To a solution of tert-butyl 4-(5-isopropoxy-2-methyl-4-nitrophenyl)-5,6-dihydropyridine-1(2H)-carboxylate (217 mg, 0.576 mmol) in dichloromethane (5 mL), trifluoroacetic acid (1 mL) was added and the reaction mixture was stirred at room temperature for 6 hr. The dichloromethane and trifluoroacetic acid were removed under vacuum and 100 mL of dichloromethane was added, washed with saturated NaHCO$_3$ solution. The water layer was extracted with dichloromethane for additional two times (100 mL each). The organic layers were combined, washed with brine, dried over Na$_2$SO$_4$ and evaporated. The residue was dissolved in dichloromethane (10 mL) and tetrahydro-4H-pyran-4-one (173 mg, 1.728 mmol), sodium triacetoxyborohydride (244 mg, 1.152 mmol) and acetic acid (69 mg, 1.152 mmol) were then added. The reaction was stirred at room temperature overnight. The reaction was quenched by adding water (80 mL), and extracted with dichloromethane (3×100 mL). The organic layers were combined, washed with brine, dried over Na$_2$SO$_4$, concentrated and purified by silica gel column chromatography with ethyl acetate/methanol (9/1, v/v) to afford the title compound of Step C (170 mg, 82% for two steps) as a yellow oil.

$^1$H NMR (400 MHz, CDCl$_3$) δ 7.63 (s, 1H), 6.83 (s, 1H), 5.62-5.59 (m, 1H), 4.58-4.56 (m, 1H), 4.11-4.01 (m, 2H), 3.43-3.28 (m, 4H), 2.78 (t, J=5.6 Hz, 2H), 2.60-2.56(m, 1H), 2.40-2.36 (m, 2H), 2.23 (s, 3H), 1.86-1.82 (m, 2H), 1.69-1.65 (m, 2H), 1.35 (d, J=6.1 Hz, 6H).

Step D: Synthesis of 2-isopropoxy-5-methyl-4-(1-(tetrahydro-2H-pyran-4-yl)-1,2,3,6-tetrahydropyridin-4-yl)aniline To a solution of 4-(5-isopropoxy-2-methyl-4-nitrophenyl)-1-(tetrahydro-2H-pyran-4-yl)-1,2,3,6-tetrahydropyridine (2.4 g, 6.66 mmol) in 30 mL of ethanol was added 4 mL of 10% HCl, followed by iron powder (2.23 g, 40 mmol). The mixture was stirred at 60° C. for 3 hr. The reaction was cooled to room temperature and the iron powder was filtered off. Ethanol was removed under reduced pressure and the title compound of Step D was obtained as pale yellow oil (2.0 g, 91% yield). MS m/z=331 [M+H].

Step E: Synthesis of 5-chloro-N$^2$-(2-isopropoxy-5-methyl-4-(1-(tetrahydro-2H-pyran-4-yl)-1,2,3,6-tetrahydropyridin-4-yl)phenyl)-N$^4$-(2-(isopropylsulfonyl)phenyl)pyrimidine-2,4-diamine 2-Isopropoxy-5-methyl-4-(1-(tetrahydro-2H-pyran-4-yl)-1,2,3,6-tetrahydropyridin-4-yl) aniline (330 mg, 1 mmol), 2,5-dichloro-N-(2-(isopropylsulfonyl)phenyl)pyrimidin-4-amine (345 mg, 1 mmol), Xantphos (58 mg, 0.1 mmol), Pd(OAc)$_2$ (11 mg, 0.05 mmol), and Cs$_2$CO$_3$ (975 mg, 3 mmol) were dissolved in anhydrous THF (20 mL). N$_2$ was bubbled through the reaction mixture for 5 min, and then the reaction vessel was sealed and heated under microwave irradiation to 150° C. for 30 min. The mixture was filtered and the filtrate concentrated under reduced pressure. After concentration, the crude product was purified by prep-HPLC (gradient from 10% to 60% acetonitrile in water) to the title compound of Step E (125 mg, 20% yield).

$^1$H NMR (400 MHz, DMSO-d$_6$) δ 9.46 (s, 1H), 8.46 (d, J=8.3 Hz, 1H), 8.27 (s, 1H), 8.06 (s, 1H), 7.85 (dd, J=8.3, 1.5 Hz, 1H), 7.66 (t, J=8.3 Hz, 1H), 7.59 (s, 1H), 7.37 (t, J=7.6 Hz, 1H), 6.73 (s, 1H), 5.57-5.50 (m, 1H), 4.58-4.54 (m, 1H), 3.96-3.87 (m, 2H), 3.47-3.43 (m, 1H), 3.31 (t, J=11.1 Hz, 2H), 3.17 (d, J=3.1 Hz, 2H), 2.70 (t, J=5.5 Hz, 2H), 2.29 (t, J=4.5 Hz, 2H), 2.07 (s, 3H), 1.78-1.74 (m, 2H), 1.49-1.45 (m, 2H), 1.23 (d, J=6.0 Hz, 6H), 1.16 (d, J=6.8 Hz, 6H).

The obtained compound was prepared as a methanesulfonate (Compound 5) for use in the following examples.

Example 2

WST Experiment

Cell plating: Anti-proliferative effects were detected by a CCK-8 (Cell Counting Kit-8) assay based on water soluble tetrazolium salt (WST). The cells were seeded in 96-well plates, and only 95 μL of complete medium was added to each negative control group. 95 μL of complete medium cell suspension was added to each well to be tested, and the cell density was (5–10)×10^4/hole.

Dosing (protection from light): In 96-well culture plates, according to the sensitivity of different cells to different drugs, the highest concentration was selected as 10 μM, and 9 concentrations were obtained by serial dilution in a ratio of 1:3.5 μL of compound was added to each well and 2-3 replicate wells were made for per concentration. After the compound was added, 96-well plates were incubated in a 5% CO$_2$ incubator at 37° C. After 72 hours of action by using 9 different concentrations of the drug with 3 fixed doses of Compound 5, the combination effect of Compound 5 and the drug was tested.

Reading: At the end of the culture, the old solution was removed from the well to be tested, and 100 μl/well CCK-8 test solution (containing 10% CCK-8, 5% FBS in the corresponding medium) was added. The plates were continuously incubated at 37° C. for 2-4 hours in a CO$_2$ incubator.

The OD values were measured using a microplate reader (SpectraMax Plus 384, Molecular Devices, LLC., US) under A450 nm. Using the average OD value of 3 replicate wells, the percentage of cell viability was calculated by the following formula:

(O.D. of test well−O.D. of blank control well)/(O.D. of cell control well−O.D. of blank control well)×100%.

IC$_{50}$ values were calculated using Graphpad Prism 6.0 software for nonlinear regression data analysis method. The results are shown in FIG. 1 and Table 1.

For combination experiments, cell viability was calculated by normalization of the mean OD values of 3 replicate wells of single drug control. The comparison of the IC$_{50}$ values obtained from the curves of combined drugs of administration and single drug of administration shows that the two compounds achieved synergistic effect (the curve of the combined drugs of administration shifted to the left).

TABLE 1

Combination of Compound 5 and EGFR inhibitor enhances inhibition effect on NCI-H1975 tumor cell proliferation

| Compound A | Compound B (EGFR inhibitor) | Compound A IC$_{50}$ | Compound B IC$_{50}$ | Combined administration IC$_{50}$ (A + B)* | IC$_{50}$ (single B)/IC$_{50}$ (A + B) |
|---|---|---|---|---|---|
| Compound 5 | AZD9291 | 3.549 ± 1.114 | 0.41 | 0.082/0.058/0.002 | 5/7/205 |
|  | afatinib |  | 0.337 | 0.119/0.135/0.136 | 2.8/2.49/2.48 |

Notation:
Each IC$_{50}$ value of the combinations corresponds to one concentration of Compound 5 (μM).

Example 3

Evaluation Method for In Vivo Pharmacodynamic Experiment

A subcutaneous xenograft tumor model of human tumor immunodeficient mice was established by cell inoculation: tumor cells in logarithmic growth phase were collected, counted, resuspended in 1×PBS, and the cell suspension concentration was adjusted to 2.5–5×10$^7$/mL. The tumor cells were inoculated subcutaneously in the right side of immunodeficient mice with a 1 mL syringe (4 gauge needle), 5–10×10$^6$/0.2 mL/mouse. All animal experiments were strictly in accordance with the specifications for the use and management of experimental animals in Gima Gene Co., Ltd. and Suzhou Ascentage Pharma Co., Ltd. The calculation of relevant parameters refers to the Chinese NMPA "Guidelines for Non-Clinical Research Techniques of Cytotoxic Anti-tumor Drugs".

Animal body weight and tumor size were measured twice weekly during the experiment. The state of the animal and the presence or absence of death were observed every day. The growth of tumor and the effects of treatment on normal behavior of animals were monitored routinely, specifically involving experimental animal activity, feeding and drinking, weight gain or loss, eyes, clothing hair and other abnormalities. The deaths and clinical symptoms observed during the experiment were recorded in the raw data. All operations for administration and measurement of mouse body weight and tumor volume were performed in a clean bench. According to the requirements of the experimental protocol, after the end of the last administration, plasma and tumor tissues were collected, weighed and photographed. The plasma and tumor samples were frozen at −80° C. for ready-to-use.

Tumor volume (TV) is calculated as: TV=a×b²/2, wherein a and b represent the length and width of the tumor to be measured, respectively.

The relative tumor volume (RTV) is calculated as: RTV=$V_t/V_1$, wherein $V_1$ is the tumor volume at the start of grouping and administration, and $V_t$ is the tumor volume measured on the t day after administration.

The evaluation index of anti-tumor activity is the relative tumor proliferation rate T/C (%), and the calculation formula thereof is: relative tumor proliferation rate T/C (%)=($T_{RTV}$/$C_{RTV}$)×100%, $T_{RTV}$ is the RTV of treatment group, $C_{RTV}$ is the RTV of solvent control group.

Tumor regression rate (%) is calculated as: the number of tumor-bearing mice which exhibit SD (stable disease), PR (partial regression) and CR (complete regression) after treatment/the total number of the mice in this group×100%.

Change of body weight (%)=(measured body weight−body weight at the start of grouping)/body weight at the start of grouping×100%.

Evaluation criteria for therapeutic efficiency: According to the Chinese NMDA "Guidelines for Non-Clinical Research Techniques of Cytotoxic Anti-tumor Drugs" (November 2006), when T/C (%) value is ≤40% and statistical analysis shows p<0.05, efficiency is confirmed. A dose of drug is considered to be severely toxic if the body weight of mouse is reduced by more than 20% or the number of drug-related deaths exceeds 20%.

According to the description by Clarke R., Issues in experimental design and endpoint analysis in the study of experimental cytotoxic agents in vivo in breast cancer and other models [J]. *Breast Cancer Research & Treatment*, 1997, 46(2-3): 255-278, synergy analysis was evaluated using the following formula: synergy factor=((A/C)×(B/C))/(AB/C); A=RTV value of drug A alone group; B=RTV value of drug B alone group; C=RTV value of the solvent control group, and AB=RTV value of the A and B combination group. Synergistic factor>1 indicates that synergy is achieved; synergy factor=1 indicates that additive effect is achieved; and synergy factor<1 indicates that antagonistic effect is achieved.

Example 4

Anti-Tumor Effect of Drug Combination of Compound 5 and EGFR Inhibitor in Human NCI-H1975 Lung Cancer Mouse Xenograft Tumor Model In in vitro cell experiments, NSCLC H1975 cells carrying $EGFR^{T790M}$ mutation was very sensitive to a combination of Compound 5 and an EGFR inhibitor (FIG. 1). Subsequently, a H1975 cell-derived mouse xenograft tumor model was established to evaluate the anti-tumor effects of Compound 5 in combination with EGFR inhibitor AZD9291 (osimertinib) or afatinib. The dosage regimens are as follows:

Compound 5: 100 mg/kg, orally, once per day, for a total of 21 days;

AZD9291: Day 1-3: 5 mg/kg, orally, once per day; Days 4-21, 2 mg/kg, orally, once per day, for a total of 21 days;

Afatinib: Days 1-7: 10 mg/kg, orally, once per day; Days 8-14: discontinuation; Days 15-21, 5 mg/kg, orally, once per day, for a total of 14 days;

The dosing regimen of each drug in the dosing regimen for the combination is the same as the dosing regimen for the single drug.

Figure 2:
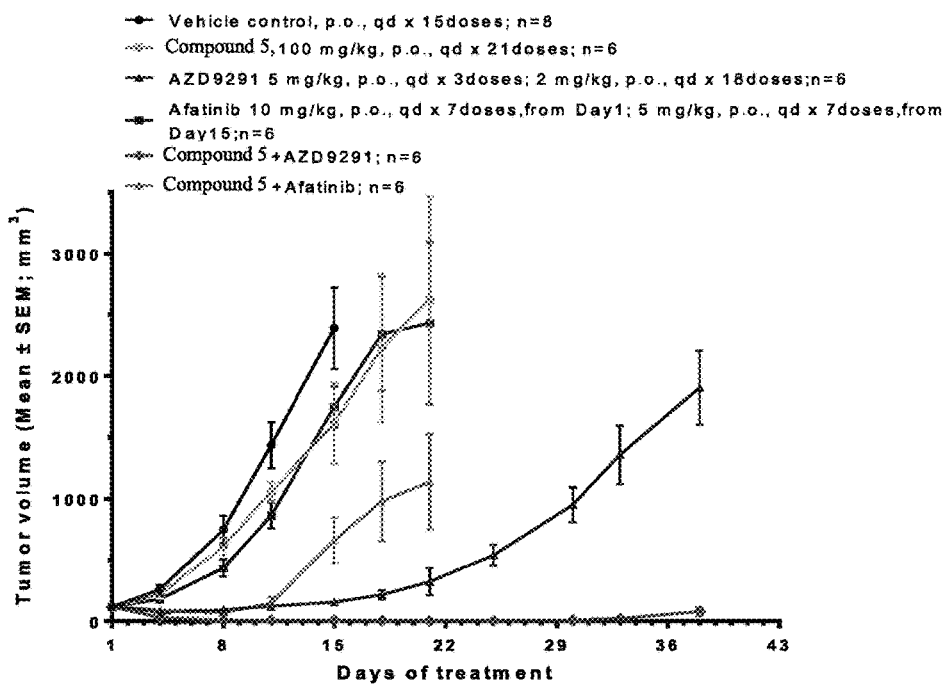
FIG. 2 shows synergistic anti-tumor effect of Compound 5 in combination with AZD9291 (osimertinib) or afatinib in a human NCI-H1975 lung cancer mouse xenograft tumor model.

As shown in FIG. 2 and Table 2, after 15 days of administration, the T/C values of single AZD9291 and its combination with Compound 5 were 6% and 0.5%, respectively; the T/C values of single afatinib and its combination with Compound 5 were 74% and 30%, respectively. The regression rate of a combination of AZD9291 and Compound 5 was 100%, in which the complete regression (CR) rate was about 33.3%, and the partial regression (PR) rate was 66.7%. After discontinuation of administration, the tumor rebound was gradually observed in the single AZD9291 group, and no tumor was observed in the combination group of AZD9291 and Compound 5.

The results showed that the anti-tumor effect of Compound 5 in combination with EGFR inhibitor was significantly superior to that of the singe drug, and synergistic effect was obtained, and Compound 5 could overcome or delay the resistance to the third-generation EGFR inhibitor osimertinib.

TABLE 2

Synergistic anti-tumor effect of Compound 5 in combination with AZD9291 (osimertinib) or afatinib in human NCI-H1975 lung cancer mouse xenograft tumor model

| Treatment | RTV on Day 15 after administration (mean ± standard error) | T/C on Day 15 after administration (%) | Synergistic factor on Day 15 after administration | Tumor status on Day 15 after administration (regression, %) |
|---|---|---|---|---|
| vehicle control | 21.0 ± 2.1 | — | | |
| Compound 5 | 13.8 ± 1.8 | 66.0 | | |
| AZD9291 | 1.4 ± 0.2*** | 6.0 | | |
| Afatinib | 15.5 ± 1.5 | 74.0 | | |
| Compound 5 + AZD9291 | 0.1 ± 0.0***&& | 0.5 | 9.2 | 2/6 CR; 4/6 PR (100%) |
| Compound 5 + afatinib | 6.3 ± 1.6*** | 30.0 | 1.63 | |

***P < 0.0001, compared to the solvent control;

&&P < 0.001, compared to the single Compound 5 group.

Example 5

Anti-Tumor Effect of Compound 5 in Combination with AZD9291 (Osimertinib) in $EGFR^{T790M}$ NCI-H1975 Xenograft Tumor Model In in vitro cell experiments, NSCLC H1975 cells carrying $EGFR^{T790M}$ mutation was very sensitive to a combination of Compound 5 and an EGFR inhibitor AZD9291 (osimertinib) (FIG. 1). Subsequently, human NSCLC H1975 derived xenograft mode was established to evaluate the anti-tumor effect of Compound 5 in combination with the EGFR inhibitor AZD9291 (osimertinib). The dosing regimen was as follows:

Compound 5: 100 mg/kg, orally, once per day, for a total of 15 days;

AZD9291: 2 mg/kg, orally, once per day, for a total of 15 days;

The dosing regimen of each drug in the dosing regimen for the combination is the same as the dosing regimen for the single drug.

Figure 3:
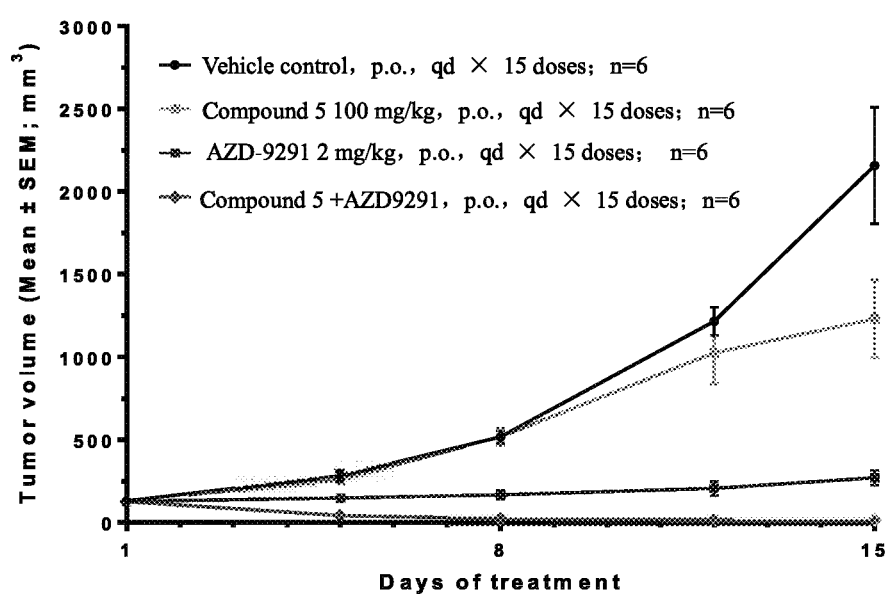
FIG. 3 shows synergistic anti-tumor effect of Compound 5 in combination with AZD9291 (osimertinib) in a human $EGFR^{T790M}$-mutant NCI-H1975 lung cancer xenograft tumor model.

As shown in FIG. 3 and Table 3, after 15 days of administration, the T/C values of single AZD9291 and its combination with Compound 5 were 12.0% and 1.0%, respectively. The regression rate of a combination of AZD9291 and compound 5 was 100%, wherein the complete regression (CR) rate was 0%, and the partial regression (PR) rate was 100%.

The results show that the anti-tumor effect obtained by a combination of Compound 5 and EGFR inhibitor was obviously superior to that obtained by the single drug, and the synergistic effect was observed.

In addition, at the end of the study, the range of weight loss in mice with weight loss was less than about 5%, and thus it was considered that no severe toxicity occurred at all doses of the administration groups.

TABLE 3

| Treatment | RTV on Day 15 after administration (mean ± standard error) | T/C on Day 15 after administration (%) | Tumor status on Day 15 after administration (regression rate, %) | Synergistic factor on Day 15 after administration |
|---|---|---|---|---|
| vehicle control | 17.0 ± 3.3 | | 0/6 CR, 0/6 PR, 0/6 SD (0%) | |
| Compound 5 | 9.6 ± 1.9 | 57.0 | 0/6CR, 0/6 PR, 0/6 SD (0%) | |
| AZD9291 | 2.1 ± 0.3 | 12.0 | 0/6 CR, 1/6 PR (17%) | |
| Compound 5 + AZD9291 | 0.1 ± 0.0* | 1.0 | 0/6 CR, 6/6 PR (100%) | 10.39 |

Example 6

Comparison of Anti-Tumor Effect Between Compound 5 in Combination with AZD9291 (Osimertinib) and FAK Selective Inhibitor Defactinib in Combination with AZD9291 (Osimertinib) in NCI-H1975 Xenograft Tumor Model In in vitro cell experiments, NSCLC H1975 cells carrying $EGFR^{T790M}$ mutation was very sensitive to some $3^{rd}$ generation of EGFR inhibitors (FIG. 1). Therefore, in this experiment, a human H1975 cell-derived xenograft tumor model was established to evaluate the anti-tumor effect of Compound 5 in combination with EGFR inhibitor AZD9291 (osimertinib), and the anti-tumor effect of FAK selective inhibitor Defactinib in combination with AZD9291 (osimertinib). The dosing regimen was as follows:

Compound 5: 50 mg/kg, orally, once per day, for a total of 22 days;

Defactinib: 50 mg/kg, orally, once per day, for a total of 22 days;

AZD9291: 2 mg/kg, orally, once per day, for a total of 22 days;

The dosing regimen of each drug in the dosing regimen for the combination is the same as the dosing regimen for the single drug.

Figure 4:
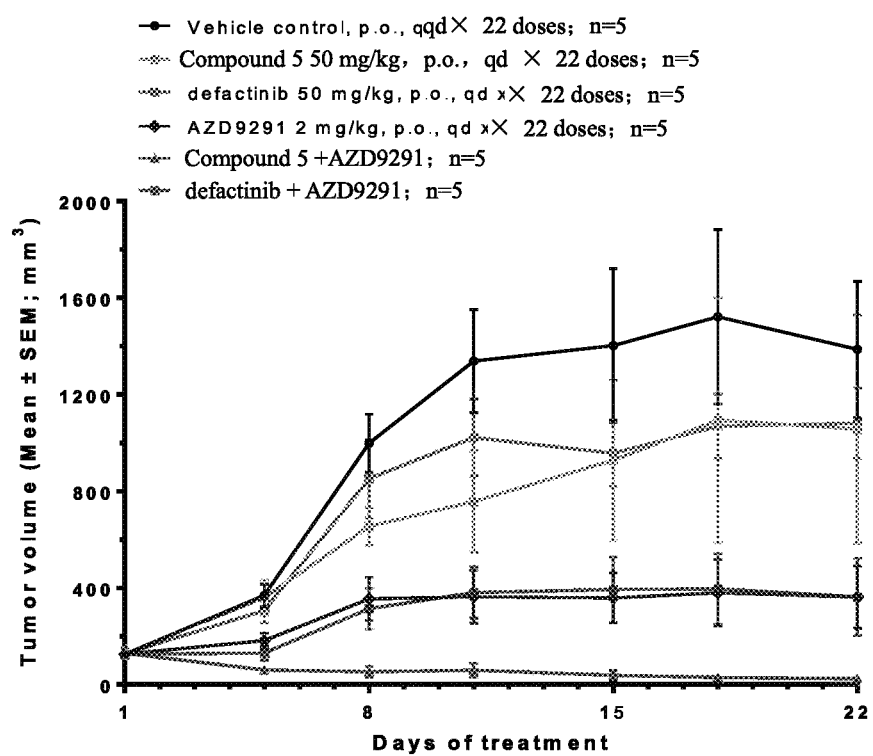
FIG. 4 shows comparison of anti-tumor effects between Compound 5 in combination with AZD9291 (osimertinib) and Defactinib in combination with AZD9291 (osimertinib) in a human NCI-H1975 xenograft tumor model.

As shown in FIG. 4 and Table 4, after 22 days of administration, the T/C values of single AZD9291 and its combination with Compound 5 were 19.8% and 1.4%, respectively. As comparison, after 22 days of administration, the T/C values of single AZD9291 and its combination with Defactinib were 19.8% and 19.8%, respectively. After day 22 of administration, the Compound 5+AZD9291 group had a synergistic factor of 12.25 and the Defactinib+AZD9291 group had a synergistic factor of 0.63. Accordingly, it was considered that the anti-tumor effect of the FAK selective inhibitor, Defactinib, was lower than that of Compound 5 when combined with AZD9291.

In addition, at the end of the study, the range of weight loss in mice with weight loss was less than about 5%, and it was considered that no severe toxicity occurred at all doses of the administration groups.

TABLE 4

| Treatment | RTV on Day 22 after administration (mean ± standard error) | T/C on Day 22 after administration (%) | Synergistic factor on Day 22 after administration |
|---|---|---|---|
| vehicle control | 13.6 ± 1.6 | | |
| Compound 5 | 9.6 ± 4.0 | 70.6 | |
| Defactinib | 8.6 ± 1.1 | 63.2 | |
| AZD9291 | 2.7 ± 0.9** | 19.8 | |
| Compound 5 + AZD9291 | 0.2 ± 0.1** | 1.4 | 12.25 |
| Defactinib + AZD9291 | 2.7 ± 1.2** | 19.8 | 0.63 |

*p < 0.05, compared to the vehicle control group;
**p < 0.01, compared with the vehicle control group

Example 7

Comparison of Anti-Tumor Effect Between Compound 5 in Combination with AZD9291 (Osimertinib) and ALKi Selective Inhibitor Ensartinib in Combination with AZD9291 (Osimertinib) in NCI-H1975 Xenograft Tumor Model In in vitro cell experiments, NSCLC H1975 cells carrying $EGFR^{T790M}$ mutation was very sensitive to some $3^{rd}$ generation of EGFR inhibitors (FIG. 1). Therefore, in this experiment, a human H1975 cell-derived mouse xenograft tumor model was established to evaluate the anti-tumor effect of Compound 5 in combination with EGFR inhibitor AZD9291 (osimertinib), and the anti-tumor effect of ALK selective inhibitors Ensartinib in combination with AZD9291 (osimertinib). The dosage regimen was as follows:

Compound 5: 50 mg/kg, orally, once per day, for a total of 21 days;

Ensartinib: 20 mg/kg, orally, once per day, for a total of 21 days;

AZD9291: 2 mg/kg, orally, once per day; for a total of 21 days;

The dosing regimen of each drug in the dosing regimen for the combination is the same as the dosing regimen for the single drug.

Figure 5:
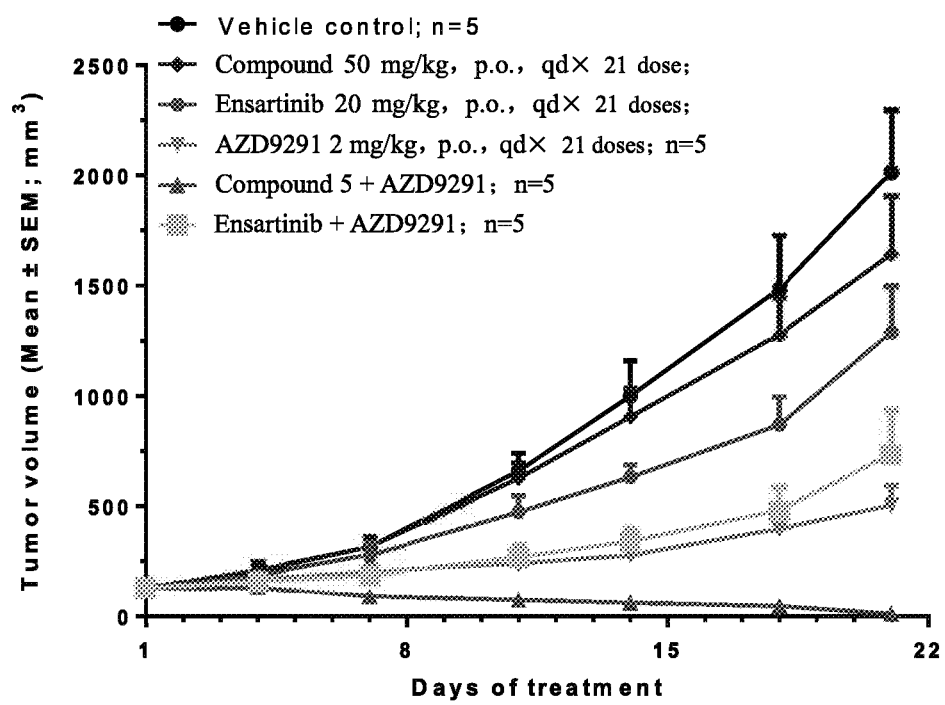
FIG. 5 shows comparison of anti-tumor effects between Compound 5 in combination with AZD9291 (osimertinib) and Ensartinib in combination with AZD9291 (osimertinib) in a human NCI-H1975 xenograft tumor model.

As shown in FIG. 5 and Table 5, after 21 days of administration, the T/C values of single AZD9291 and its combination with Compound 5 were 24.4% and 0%, respectively. As comparison, after 21 days of administration, the T/C values of single AZD9291, its combination with Ensartinib, and its combination with Compound 5 were 24.4%, 42.2% and 0, respectively. The regression rate of of AZD9291 in combination with Compound 5 was 100%, wherein the complete regression rate (CR) was 80%, and the partial regression rate (PR) was 20%. After 21 days of administration, the compound 5+AZD9291 group had a synergistic factor of 44.6, and the Ensartinib+AZD9291 group had synergistic factor of 0.43. Accordingly, it was considered that when combined with AZD9291, the anti-tumor effect of the ALK selective inhibitor Ensartinib is lower than that of Compound 5.

In addition, at the end of the study, the range of weight loss in mice with weight loss was less than about 5%, and it was considered that no severe toxicity occurred at all doses of the administration groups.

TABLE 5

| Treatment | RTV on Day 21 after administration (mean ± standard error) | T/C on Day 21 after administration (%) | Synergistic factor on Day 21 after administration | Tumor status on Day 21 after administration (regression, %) |
| --- | --- | --- | --- | --- |
| vehicle control | 16.0 ± 2.07 | — | — | — |
| Compound 5 | 12.8 ± 1.5& | 80 | — | — |
| Ensartinib | 9.5 ± 1.1& | 61.3 | — | — |
| AZD9291 | 3.9 ± 0.7*#$ | 24.4 | — | — |
| Compound 5 + AZD9291 | 0.07 ± 0.07**##$$& | 0.00 | 44.6 | 4/5 CR, 1/5 PR, ORR (overall response rate) 100% |
| Ensartinib + AZD9291 | 5.4 ± 0.9*#& | 42.2 | 0.43 | — |

*$p < 0.05$,
**$p < 0.01$, compared with the vehicle control group;
$p < 0.05$,
$p < 0.01$, compared with the Compound 5 group;
$$p < 0.05$,
$$$p < 0.01$, compared with the Ensartinib group;
&$p < 0.05$ compared with the Compound 5 + AZD9291 group;
synergistic factor >1, synergistic effect;
synergistic factor = 1, additive;
synergistic factor <1, antagonism

Example 8

Comparison of Anti-Tumor Effects Between Compound 5 in Combination with Avitinib and ALK Selective Inhibitor Ensartinib in Combination with Avitinib in NCI-H1975 Xenograft Tumor Model In in vitro cell experiments, NSCLC H1975 cellscarrying $EGFR^{T790M}$ mutation was very sensitive to some $3^{rd}$ generation of EGFR inhibitors (FIG. 1). Therefore, in this experiment, a human H1975 cell-derived mouse xenograft tumor model was established to evaluate the anti-tumor effect of Compound 5 in combination with EGFR inhibitor Avitinib, and the anti-tumor effect of ALK selective inhibitors Ensartinib in combination with EGFR inhibitor Avitinib. The dosage regimen was as follows:

Compound 5: 50 mg/kg, orally, once per day, for a total of 21 days;

Ensartinib: 20 mg/kg, orally, once per day, for a total of 21 days;

Avitinib: 10 mg/kg, orally, once per day; for a total of 21 days;

The dosing regimen of each drug in the dosing regimen for the combination is the same as the dosing regimen for the single drug.

Figure 6:
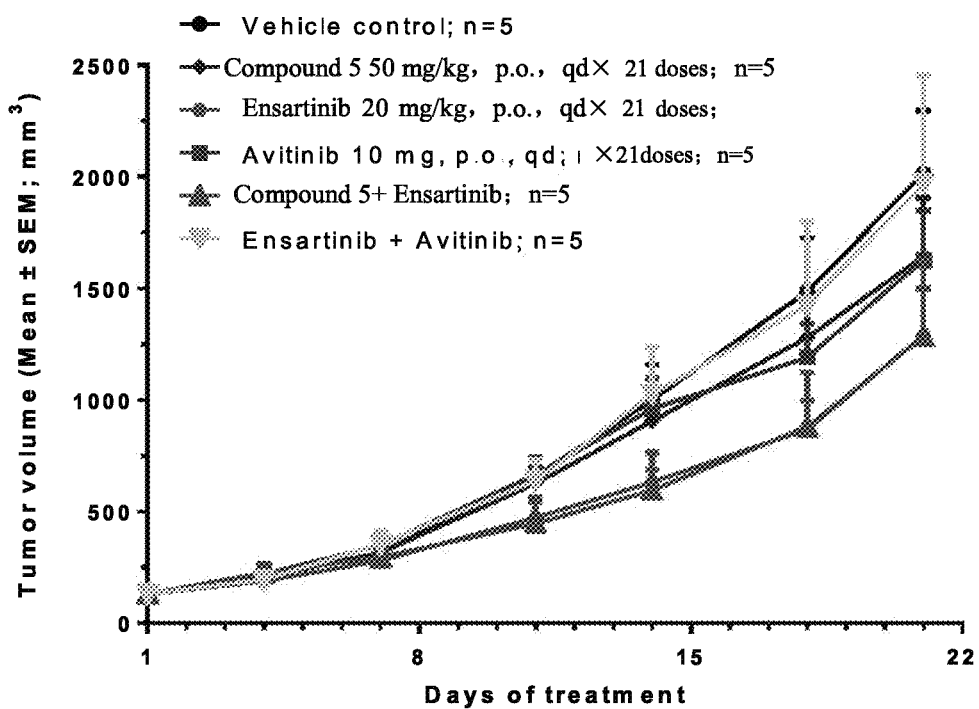
FIG. 6 shows comparison of anti-tumor effects between Compound 5 in combination with Avitinib and Ensartinib in combination with Avitinib in a human NCI-H1975 xenograft tumor model.

As shown in FIG. 6 and Table 6, after 21 days of administration, the T/C values of Avitinib and its combination with Compound 5 were 83.1% and 56.9%, respectively. As comparison, after 21 days of administration, the T/C values of single Avitinib and its combination with Ensartinib were 83.1% and 94.2%, respectively. After 21 days of administration, the Compound 5+Avitinib group had a synergistic factor of 1.17; and the Ensartinib+Avitinib group had a synergistic factor of 0.54. Accordingly, it was considered that, when combined with Avitinib, the anti-tumor effect of the ALK selective inhibitor Ensartinib was lower than that of Compound 5.

In addition, at the end of the study, the body weight in mice was not significantly reduced, and it was considered that no severe toxicity occurred at all doses of the administration groups.

effect of Compound 5 in combination with AZD9291 (osimertinib), and the anti-tumor effect of Compound 5 in combination with EGFR inhibitor Avitinib. The dosage regimen was as follows:

Compound 5: 50 mg/kg, orally, once per day, for a total of 15 days;

AZD9291: 2 mg/kg, orally, once per day, for a total of 15 days;

Avitinib: 10 mg/kg, orally, once per day; for a total of 15 days;

The dosing regimen of each drug in the dosing regimen for the combination is the same as the dosing regimen for the single drug.

Figure 7:
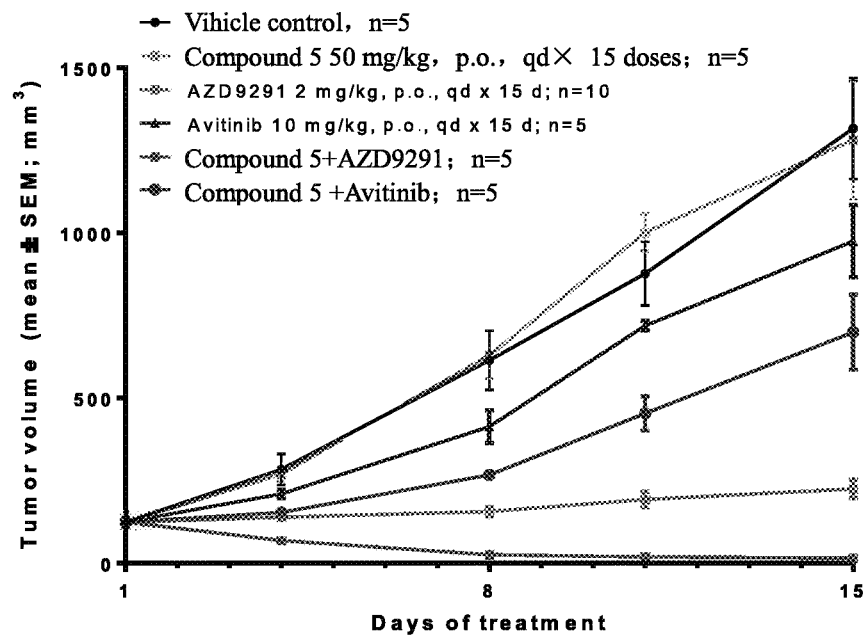
FIG. 7 shows comparison of anti-tumor effects between Compound 5 in combination with AZD9291 (osimertinib) and Compound 5 in combination with Avitinib in a human NCI-H1975 xenograft tumor model.
Figure 7:
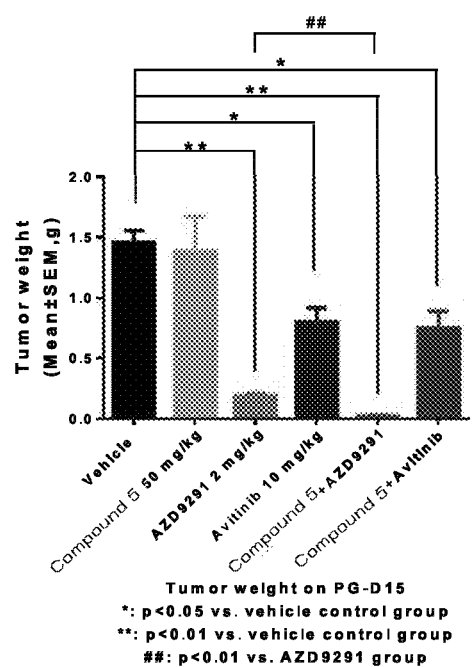

As shown in FIG. 7 and Table 7, after 15 days of administration, the T/C values of single Compound 5 and its combination with AZD9291 (osimertinib) were 95.6% and

TABLE 6

| Treatment | RTV on Day 21 after administration (mean ± standard error) | T/C on Day 21 after administration (%) | Synergistic factor on Day 21 after administration | Tumor status on Day 21 after administration (regression, %) |
| --- | --- | --- | --- | --- |
| vehicle control | 16.0 ± 2.07 | — | — | — |
| Compound 5, 50 mg/kg | 12.8 ± 1.5 | 80 | — | — |
| Ensartinib, mg/kg 20 | 9.5 ± 1.1 | 61.3 | — | — |
| Avitinib | 13.29 ± 2.65 | 83.1 | — | — |
| Compound 5 + Avitinib | 9.1 ± 1.7 | 56.9 | 1.17 | — |
| Ensartinib + Avitinib | 14.5 ± 2.2 | 94.2 | 0.54 | — |

*$p < 0.05$,
**$p < 0.01$, compared with the vehicle control group;
$p < 0.05$,
$p < 0.01$, compared with the Compound 5 group;
$$p < 0.05$,
$$$p < 0.01$, compared with the Ensartinib group;
&$p < 0.05$ compared with the Compound 5 + AZD9291 group;
synergistic factor >1, synergistic effect;
synergistic factor = 1, additive;
synergistic factor <1, antagonism Example 9

Comparison of Anti-Tumor Effects Between Compound 5 in Combination with AZD9291 (Osimertinib) and Compound 5 in Combination with Avitinib in NCI-H1975 Xenograft Tumor Model In in vitro cell experiments, NSCLC H1975 cells carrying $EGFR^{T790M}$ mutation was very sensitive to some $3^{rd}$ generation of EGFR inhibitors (FIG. 1). Therefore, in this experiment, a human H1975 cell-derived mouse xenograft tumor model was established to evaluate the anti-tumor 1.2%, respectively. As comparison, after 15 days of administration, the T/C values of single Compound 5 and its combination with Avitinib were 95.6% and 51.7%, respectively. After 15 days of administration, the Compound 5+AZD9291 group had a synergistic factor of 13.66; and the Compound 5+Avitinib group had a synergistic factor of 1.34. Accordingly, it was considered that both a combination of Compound 5 with AZD9291 and a combination of Compound 5 with Avitinib showed anti-tumor effects, while a combination of Compound 5 (osimertinib) had more potent anti-tumor effect.

TABLE 7

| Treatment | RTV on Day 11 after administration (mean ± standard error) | T/C on Day 11 after administration (%) | Synergistic factor on Day 11 after administration | Tumor status on Day 11 after administration (regression, %) | RTV on Day 15 after administration (mean ± standard error) | T/C on Day 15 after administration (%) | Synergistic factor on Day 15 after administration | Tumor status on Day 15 after administration (regression, %) |
| --- | --- | --- | --- | --- | --- | --- | --- | --- |
| vehicle control | 7.2 ± 0.5 | — | — | — | 10.8 ± 0.8 | — | — | — |
| Compound 5, 50 mg/kg | 8.2 ± 0.5 | 113.8 | — | — | 10.3 ± 1.1 | 95.6 | — | — |

TABLE 7-continued

| Treatment | RTV on Day 11 after administration (mean ± standard error) | T/C on Day 11 after administration (%) | Synergistic factor on Day 11 after administration | Tumor status on Day 11 after administration (regression, %) | RTV on Day 15 after administration (mean ± standard error) | T/C on Day 15 after administration (%) | Synergistic factor on Day 15 after administration | Tumor status on Day 15 after administration (regression, %) |
|---|---|---|---|---|---|---|---|---|
| AZD9291, 2 mg/kg | 1.6 ± 0.3 | 1.6** | — | — | 1.8 ± 0.2** | 16.8 | — | — |
| Avitinib, 10 mg/kg | 5.9 ± 0.4 | 82.0 | — | — | 7.8 ± 0.7 | 72.4 | — | — |
| Compound 5 + AZD9291 | 0.2 ± 0.0 | 2.1**###$$$ | 11.92 | 5/5 PR | 0.1 ± 0.0**##$$$ | 1.2 | 13.66 | 5/5 PR |
| Compound 5 + Avitinib | 3.7 ± 0.4 | 51.1**##& | 1.83 | — | 5.6 ± 0.7* | 51.7 | 1.34 | — |

**$p < 0.01$, compared with the vehicle control group,
***$p < 0.001$, compared with the vehicle control group;
$p < 0.01$, compared with the Compound 5 group,
$p < 0.001$, compared with the Compound 5 group;
$$p < 0.05$, compared with the AZD9291 group,
$$$p < 0.01$, compared with the AZD9291 group;
&$p < 0.05$, compared with the Avitinib group;
synergistic factor >1, synergistic effect;
synergistic factor = 1, additive;
synergistic factor <1, antagonism Various modifications of the invention in addition to those described herein will be apparent to those skilled in the art. Such modifications are also intended to fall within the scope of the appended claims. Each of the references (including all of patents, patent applications, journal articles, books, and any other publications) cited in this application are hereby incorporated by reference in their entirety.

What is claimed is:

1. A method for treating or suppressing a cancer, reducing its severity, lowering its risk or inhibiting its metastasis in an individual, comprising administering to the individual a therapeutically effective amount of an ALK inhibitor, or a pharmaceutically acceptable salt or solvate thereof, and a therapeutically effective amount of an EGFR inhibitor, or a pharmaceutically acceptable salt or solvate thereof, wherein (i) the cancer is bladder cancer, breast cancer cervical cancer, colon cancer, esophageal cancer, esophageal squamous cell carcinoma, head and neck cancer, liver cancer, lung cancer, melanoma, myeloma, rhabdomyosarcoma, inflammatory myofibroblastic tumor, neuroturbo chargeoma, pancreatic cancer, prostate cancer kidney cancer, renal cell carcinoma, sarcoma, skin cancer, gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, acute myeloid leukemia, acute lymphoblastic leukemia, diffuse large B-cell lymphoma, follicular lymphoma, chronic lymphocytic leukemia, or chronic myeloid leukemia; and (ii) the ALK inhibitor is a compound of Formula I:

wherein:

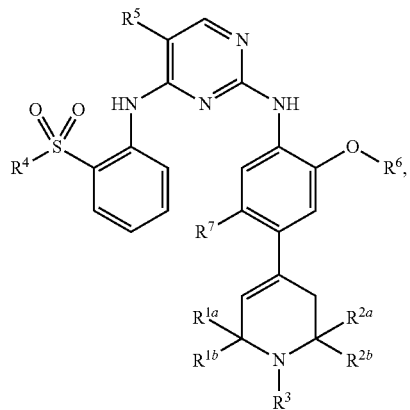

I $R^{1a}$ and $R^{1b}$ are independently selected from the group consisting of hydrogen, $C_{1-6}$ alkyl, and $C_{3-8}$ cycloalkyl;

$R^{2a}$ and $R^{2b}$ are independently selected from the group consisting of hydrogen, $C_{1-6}$ alkyl, and $C_{3-8}$ cycloalkyl;

$R^3$ is selected from the group consisting of hydrogen, $C_{1-6}$ alkyl, $C_{3-6}$ cycloalkyl, and 4- to 8-membered heterocyclyl, $R^4$ is selected from the group consisting of $C_{1-4}$ alkyl and $C_{3-6}$ cycloalkyl;

$R^5$ is halo;

$R^6$ is selected from the group consisting of $C_{1-4}$ alkyl and $C_{3-6}$ cycloalkyl; and $R^7$ is selected from the group consisting of hydrogen, $C_{1-4}$ alkyl, and $C_{3-6}$ cycloalkyl, with proviso that when $R^{1a}$, $R^{1b}$, $R^{2a}$, and $R^{2b}$ are each hydrogen, then $R^3$ is selected from the group consisting of $C_{3-6}$ cycloalkyl and 4- to 8-membered heterocyclyl.

2. The method according to claim 1, wherein the ALK inhibitor is a compound of Formula II:

wherein:

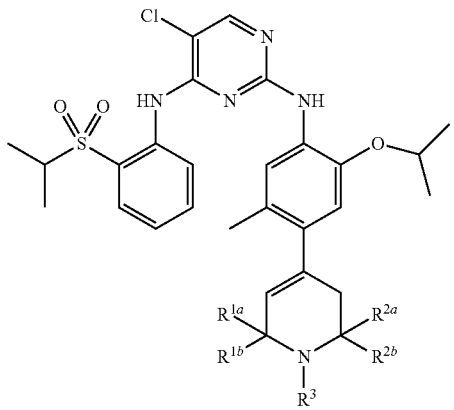

II

R$^{1a}$ and R$^{1b}$ are independently selected from the group consisting of hydrogen, C$_{1-4}$ alkyl, and C$_{3-6}$ cycloalkyl;

R$^{2a}$ and R$^{2b}$ are independently selected from the group consisting of hydrogen, C$_{1-4}$ alkyl, and C$_{3-6}$ cycloalkyl; and R$^3$ is selected from the group consisting of hydrogen, C$_{1-4}$ alkyl, C$_{3-6}$ cycloalkyl, and 4- to 8-membered heterocyclyl, or a pharmaceutically acceptable salt or solvate thereof.

3. The method according claim 1, wherein the ALK inhibitor is a compound of Formula III,

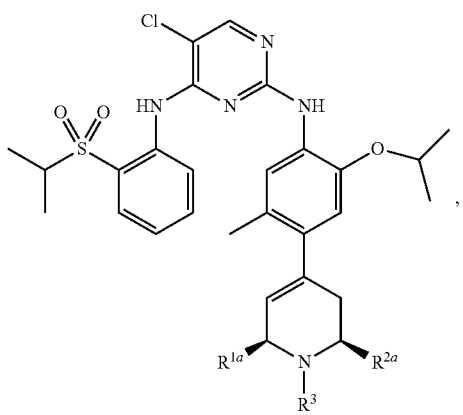

III wherein:

R$^{1a}$ and R$^{2a}$ are each independently selected from the group consisting of C$_{1-4}$ alkyl, and C$_{3-6}$ cycloalkyl; and the compound has an enantiomeric excess of about 90% or more, or a pharmaceutically acceptable salt or solvate thereof.

4. The method according to claim 1, wherein the ALK inhibitor is a compound of Formula IV:

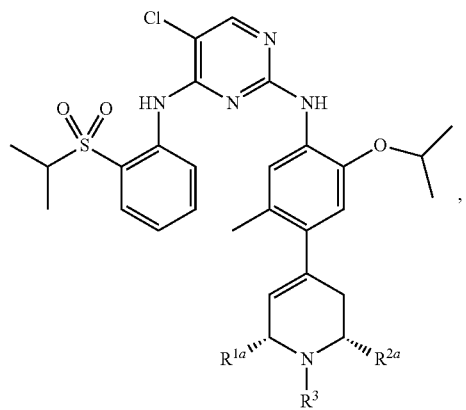

IV wherein:

R$^{1a}$ and R$^{2a}$ are each independently selected from the group consisting of C$_{1-4}$ alkyl, and C$_{3-6}$ cycloalkyl; and the compound has an enantiomeric excess of about 90% or more, or a pharmaceutically acceptable salt or solvate thereof.

5. The method according to claim 1, wherein the ALK inhibitor is a compound of Formula V:

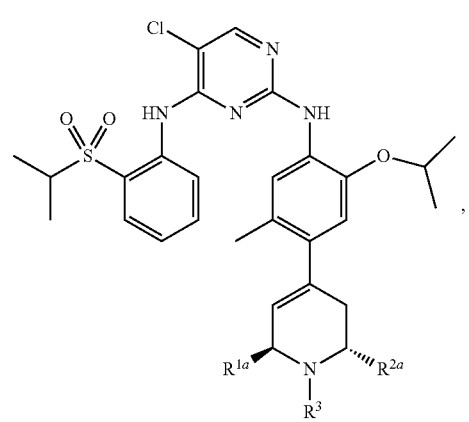

V wherein:

R$^{1a}$ and R$^{2a}$ are each independently selected from the group consisting of C$_{1-4}$ alkyl, and C$_{3-6}$ cycloalkyl; and the compound has an enantiomeric excess of about 90% or more, or a pharmaceutically acceptable salt or solvate thereof.

6. The method according to claim 1, wherein the ALK inhibitor is a compound of Formula VI:

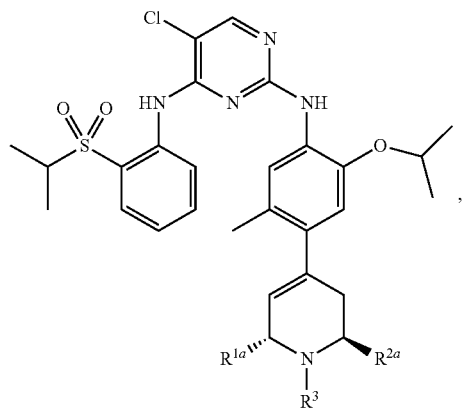

VI wherein:
R$^{1a}$ and R$^{2a}$ are each independently selected from the group consisting of C$_{1-4}$ alkyl, and C$_{3-6}$ cycloalkyl; and
the compound has an enantiomeric excess of about 90% or more,
or a pharmaceutically acceptable salt or solvate thereof.

7. The method according to claim 1, wherein the ALK inhibitor is:

| No. | Structure | Name |
|---|---|---|
| 1 | 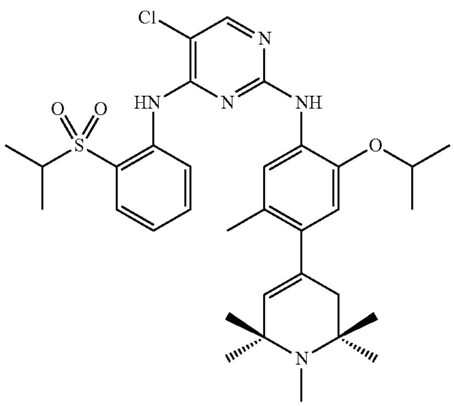 | 5-chloro-N$^2$-(2-isopropoxy-5-methyl-4-(1,2,2,6,6-pentamethyl-1,2,3,6-tetrahydropyridin-4-yl)phenyl)-N$^4$-(2-(isopropoylsulfonyl)phenyl)pyrimidine-2,4-diamine; |
| 2 | 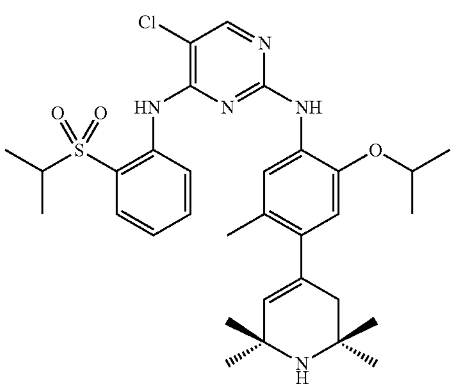 | 5-chloro-N$^2$-(2-isopropoxy-5-methyl-4-(2,2,6,6-tetramethyl-1,2,3,6-tetrahydropyridin-4-yl)phenyl)-N$^4$-(2-(isopropylsulfonyl)phenyl)pyrimidine-2,4-diamine; |
| 3 | 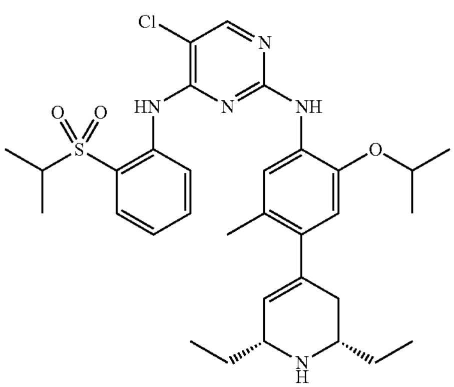 [SMILES: CC[C@H]1CC(c2cc(OC(C)C)c(Nc3ncc(Cl)c(Nc4ccccc4S(=O)(=O)C(C)C)n3)cc2C)=C[C@@H](CC)N1] | 5-chloro-N$^2$-(4-((cis)-2,6-diethyl-1,2,3,6-tetrahydropyridin-4-yl)-2-isopropoxy-5-methylphenyl)-N$^4$-(2-(isopropylsulfonyl)phenyl)pyrimidine-2,4-diamine; |

| No. | Structure | Name |
| --- | --- | --- |
| 4 | 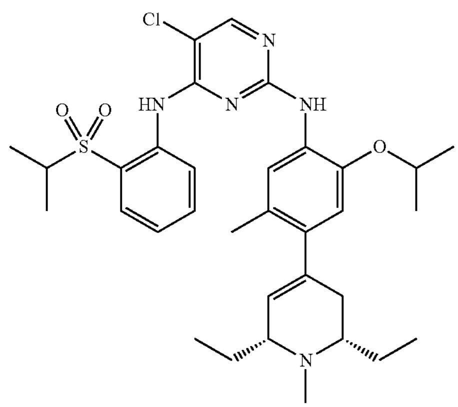 [SMILES: CC[C@H]1CC(c2cc(OC(C)C)c(Nc3ncc(Cl)c(Nc4ccccc4S(=O)(=O)C(C)C)n3)cc2C)=C[C@@H](CC)N1C] | 5-chloro-N²-(4-((cis)-2,6-diethyl-1-methyl-1,2,3,6-tetrahydropyridin-4-yl)-2-isopropoxy-5-methylphenyl)-N⁴-(2-(isopropylsulfonyl)phenyl)pyrimidine-2,4-diamine; |
| 5 | 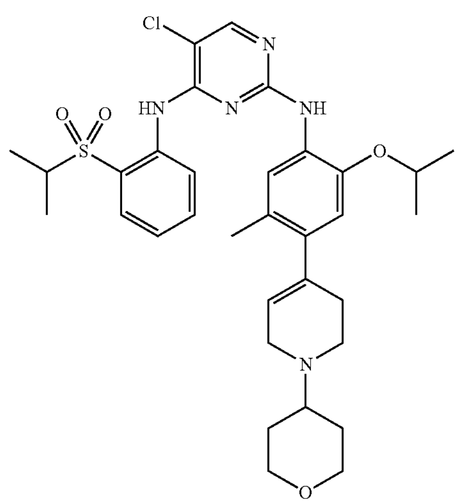 [SMILES: Cc1cc(Nc2ncc(Cl)c(Nc3ccccc3S(=O)(=O)C(C)C)n2)c(OC(C)C)cc1C1=CCN(C2CCOCC2)CC1] | 5-chloro-N²-(2-isopropoxy-5-methyl-4-(1-(tetrahydro-2H-pyran-4-yl)-1,2,3,6-tetrahydropyridin-4-yl)phenyl)-N⁴-(2-(isopropylsulfonyl)phenyl)pyrimidine-2,4-diamine; |
| 6 | 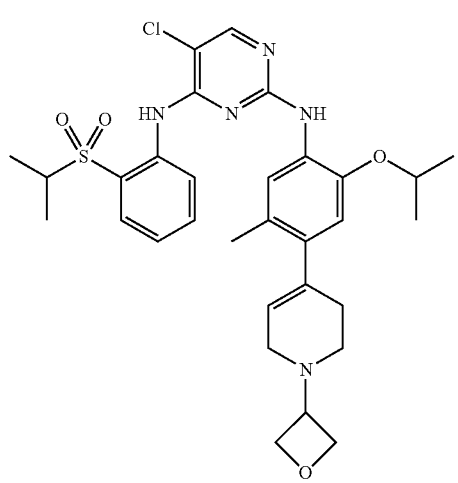 [SMILES: Cc1cc(Nc2ncc(Cl)c(Nc3ccccc3S(=O)(=O)C(C)C)n2)c(OC(C)C)cc1C1=CCN(C2COC2)CC1] | 5-chloro-N²-(2-isopropoxy-5-methyl-4-(1-(oxetan-3-yl)-1,2,3,6-tetrahydropyridin-4-yl)phenyl)-N⁴-(2-(isopropylsulfonyl)phenyl)pyrimidine-2,4-diamine; |

| No. | Structure | Name |
|---|---|---|
| 7 | 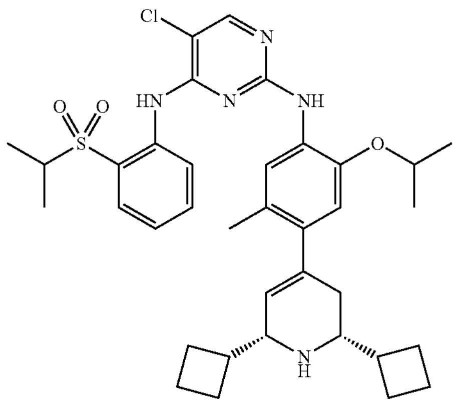 | 5-chloro-$N^2$-(4-((cis)-2,6-dicyclobutyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 8 | 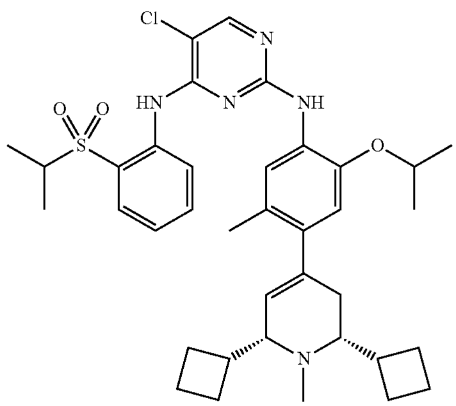 [SMILES: Cc1cc(Nc2ncc(Cl)c(Nc3ccccc3S(=O)(=O)C(C)C)n2)c(OC(C)C)cc1C1=C[C@@H](C2CCC2)N(C)[C@@H](C2CCC2)C1] | 5-chloro-$N^2$-(4-((cis)-2,6-dicyclobutyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 9 | 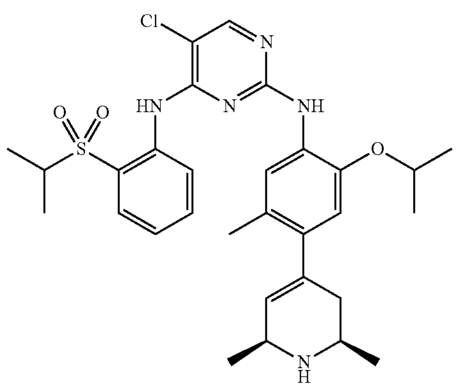 [SMILES: Cc1cc(Nc2ncc(Cl)c(Nc3ccccc3S(=O)(=O)C(C)C)n2)c(OC(C)C)cc1C1=C[C@H](C)N[C@H](C)C1] | 5-chloro-$N^2$-(4-((cis)-2,6-dimethyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 10 | 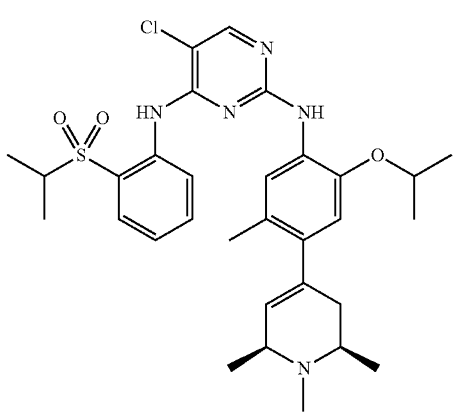 [SMILES: Cc1cc(Nc2ncc(Cl)c(Nc3ccccc3S(=O)(=O)C(C)C)n2)c(OC(C)C)cc1C1=C[C@H](C)N(C)[C@H](C)C1] | 5-chloro-$N^2$-(2-isopropoxy-5-methyl-4-((cis)-1,2,6-trimethyl-1,2,3,6-tetrahydropyridin-4-yl)phenyl)-$N^4$-(2-(isopropylsulfonyl)phenyl)pyrimidine-2,4-diamine; |

| No. | Structure | Name |
|---|---|---|
| 11 | 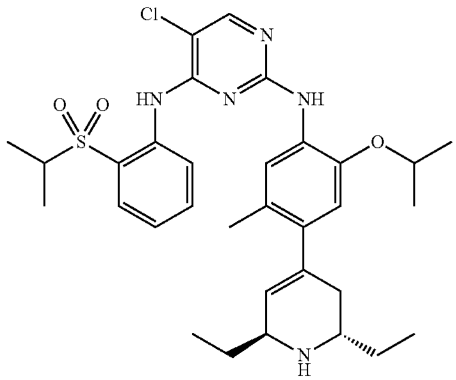 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1] | 5-chloro-$N^2$-(4-((trans)-2,6-diethyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 12 | 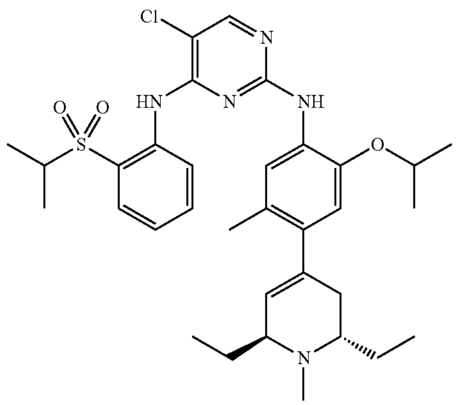 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C] | 5-chloro-$N^2$-(4-((trans)-2,6-diethyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 13 | 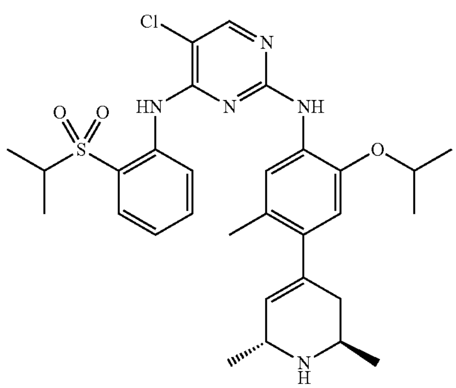 [SMILES: Cc1cc(Nc2ncc(Cl)c(Nc3ccccc3S(=O)(=O)C(C)C)n2)c(OC(C)C)cc1C1=C[C@@H](C)N[C@H](C)C1] | 5-chloro-$N^2$-(4-((trans)-2,6-dimethyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 14 | 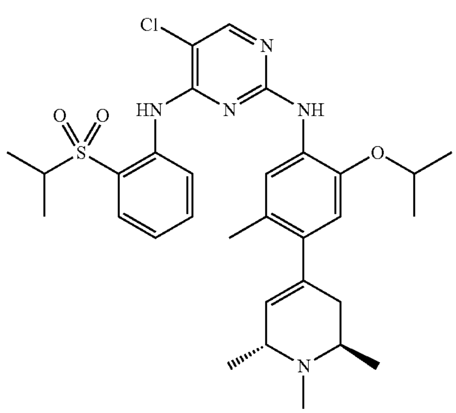 [SMILES: Cc1cc(Nc2ncc(Cl)c(Nc3ccccc3S(=O)(=O)C(C)C)n2)c(OC(C)C)cc1C1=C[C@@H](C)N(C)[C@H](C)C1] | 5-chloro-$N^2$-(2-isopropoxy-5-methyl-4-((trans)-1,2,6-trimethyl-1,2,3,6-tetrahydropyridin-4-yl)phenyl)-$N^4$-(2-(isopropylsulfonyl)phenyl)pyrimidine-2,4-diamine; |

| No. | Structure | Name |
|---|---|---|
| 15 | 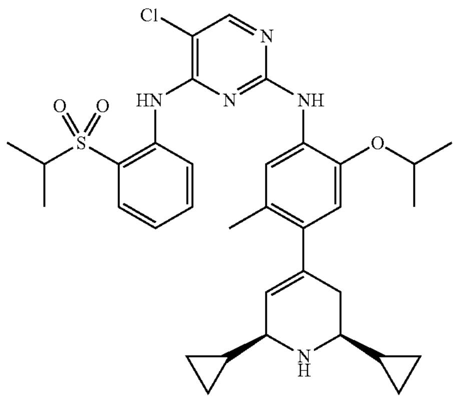 [SMILES: Cc1cc(Nc2ncc(Cl)c(Nc3ccccc3S(=O)(=O)C(C)C)n2)c(OC(C)C)cc1C1=C[C@H](C2CC2)N[C@H](C2CC2)C1] | 5-chloro-$N^2$-(4-((cis)-2,6-dicyclopropyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 16 | 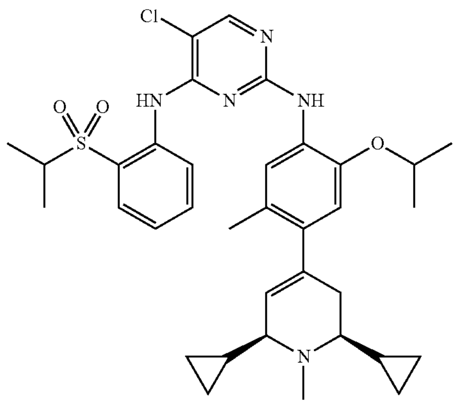 [SMILES: Cc1cc(Nc2ncc(Cl)c(Nc3ccccc3S(=O)(=O)C(C)C)n2)c(OC(C)C)cc1C1=C[C@H](C2CC2)N(C)[C@H](C2CC2)C1] | 5-chloro-$N^2$-(4-((cis)-2,6-dicyclopropyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 17 | 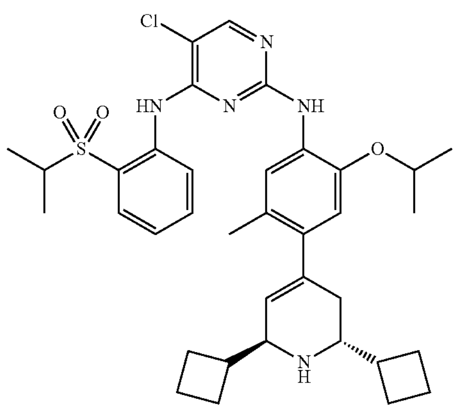 [SMILES: Cc1cc(Nc2ncc(Cl)c(Nc3ccccc3S(=O)(=O)C(C)C)n2)c(OC(C)C)cc1C1=C[C@H](C2CCC2)N[C@@H](C2CCC2)C1] | 5-chloro-$N^2$-(4-((trans)-2,6-dicyclobutyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 18 | 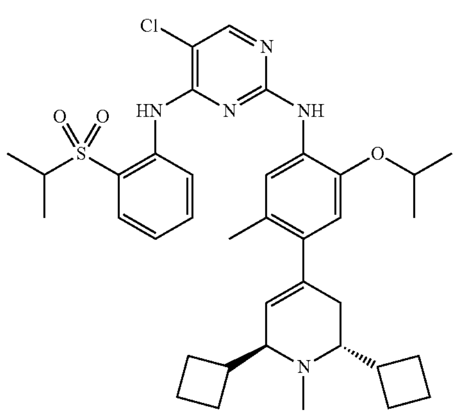 [SMILES: Cc1cc(Nc2ncc(Cl)c(Nc3ccccc3S(=O)(=O)C(C)C)n2)c(OC(C)C)cc1C1=C[C@H](C2CCC2)N(C)[C@@H](C2CCC2)C1] | 5-chloro-$N^2$-(4-((trans)-2,6-dicyclobutyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |

| No. | Structure | Name |
|---|---|---|
| 19 | 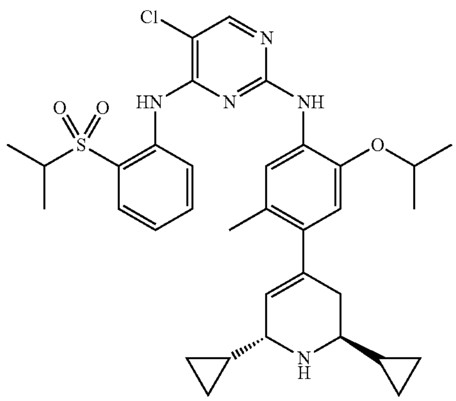 [SMILES: Cc1cc(Nc2ncc(Cl)c(Nc3ccccc3S(=O)(=O)C(C)C)n2)c(OC(C)C)cc1C1=C[C@@H](C2CC2)N[C@H](C2CC2)C1] | 5-chloro-$N^2$-(4-((trans)-2,6-dicyclopropyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 20 | 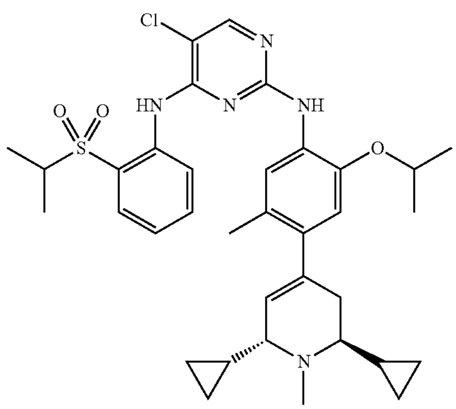 [SMILES: Cc1cc(Nc2ncc(Cl)c(Nc3ccccc3S(=O)(=O)C(C)C)n2)c(OC(C)C)cc1C1=C[C@@H](C2CC2)N(C)[C@H](C2CC2)C1] | 5-chloro-$N^2$-(4-((trans)-2,6-dicyclopropyl-1-methyl-1,2,3,6-tetrahydropyridin-4-yl)-2-isopropoxy-5-methylphenyl)-$N^4$-(2-(isopropylsulfonyl)phenyl)pyrimidine-2,4-diamine; |
| 21 | 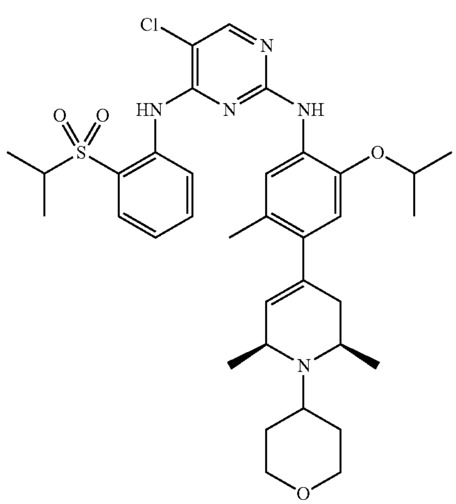 [SMILES: Cc1cc(Nc2ncc(Cl)c(Nc3ccccc3S(=O)(=O)C(C)C)n2)c(OC(C)C)cc1C1=C[C@H](C)N(C2CCOCC2)[C@H](C)C1] | 5-chloro-$N^2$-(4-((cis)-2,6-dimethyl-1-(tetrahydro-2H-pyran-4-yl)-1,2,3,6-tetrahydropyridin-4-yl)-2-isopropoxy-5-methylphenyl)-$N^4$-(2-(isopropylsulfonyl)phenyl)pyrimidine-2,4-diamine; |

| No. | Structure | Name |
|---|---|---|
| 22 | 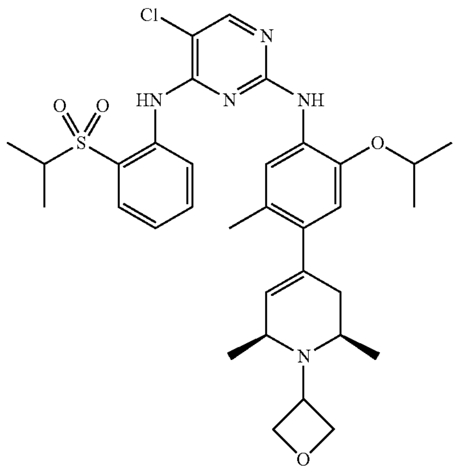 [SMILES: Cc1cc(Nc2ncc(Cl)c(Nc3ccccc3S(=O)(=O)C(C)C)n2)c(OC(C)C)cc1C1=C[C@H](C)N(C2COC2)[C@H](C)C1] | 5-chloro-$N^2$-(4-((cis)-2,6-dimethyl-1-(oxetan-3-yl)-1,2,3,6-tetrahydropyridin-4-yl)-2-isopropoxy-5-methylphenyl)-$N^4$-(2-(isopropylsulfonyl)phenyl)pyrimidine-2,4-diamine; |
| 23 | 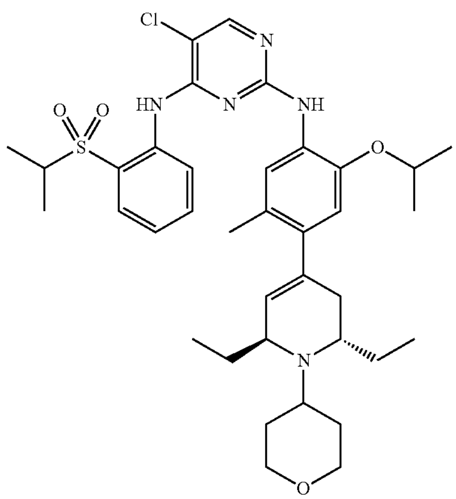 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C1CCOCC1] | 5-chloro-$N^2$-(4-((trans)-2,6-diethyl-1-(tetrahydro-2H-pyran-4-yl)-1,2,3,6-tetrahydropyridin-4-yl)-2-isopropoxy-5-methylphenyl)-$N^4$-(2-(isopropylsulfonyl)phenyl)pyrimidine-2,4-diamine; |
| 24 | 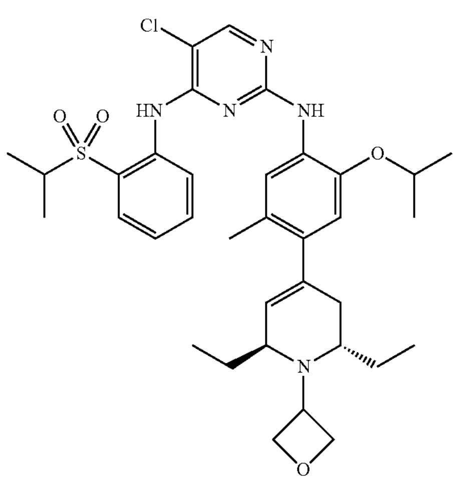 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C1COC1] | 5-chloro-$N^2$-(4-((2S,6S)-2,6-diethyl-1-(oxetan-3-yl)-1,2,3,6-tetrahydropyridin-4-yl)-2-isoproxy-5-methylphenyl)-$N^4$-(2-(isopropylsulfonyl)phenyl)pyrimidine-2,4-diamine; |

| No. | Structure | Name |
| --- | --- | --- |
| 25 | 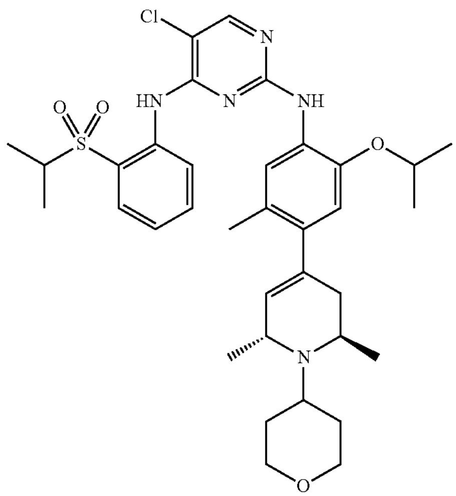 [SMILES: Cc1cc(Nc2ncc(Cl)c(Nc3ccccc3S(=O)(=O)C(C)C)n2)c(OC(C)C)cc1C1=C[C@@H](C)N(C2CCOCC2)[C@H](C)C1] | 5-chloro-$N^2$-(4-((trans)-2,6-dimethyl-1-(tetrahydro-2H-pyran-4-yl)-1,2,3,6-tetrahydropyridin-4-yl)-2-isopropoxy-5-methylphenyl)-$N^4$-(2-(isopropylsulfonyl)phenyl)pyrimidine-2,4-diamine; |
| 26 | 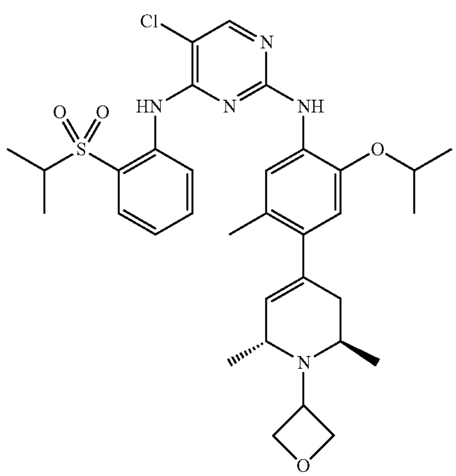 [SMILES: Cc1cc(Nc2ncc(Cl)c(Nc3ccccc3S(=O)(=O)C(C)C)n2)c(OC(C)C)cc1C1=C[C@@H](C)N(C2COC2)[C@H](C)C1] | 5-chloro-$N^2$-(4-((trans)-2,6-dimethyl-1-(oxetan-3-yl)-1,2,3,6-tetrahydropyridin-4-yl)-2-isopropoxy-5-methylphenyl)-$N^4$-(2-(isopropylsulfonyl)phenyl)pyrimidine-2,4-diamine; |
| 27 | 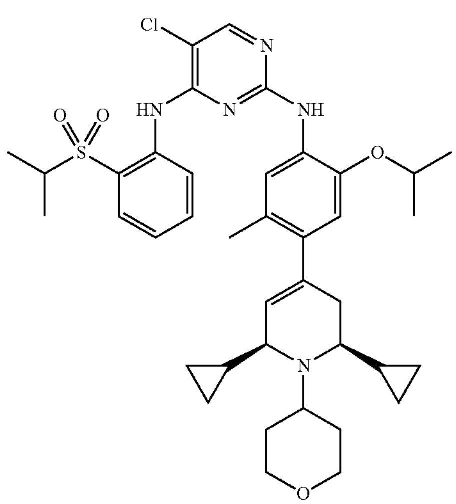 [SMILES: Cc1cc(Nc2ncc(Cl)c(Nc3ccccc3S(=O)(=O)C(C)C)n2)c(OC(C)C)cc1C1=C[C@H](C2CC2)N(C2CCOCC2)[C@H](C2CC2)C1] | 5-chloro-$N^2$-(4-((cis)-2,6-dicyclopropyl-1-(tetrahydro-2H-pyran-4-yl)-1,2,3,6-tetrahydropyridin-4-yl)-2-isopropoxy-5-methylphenyl)-$N^4$-(2-(isopropylsulfonyl)phenyl)pyrimidine-2,4-diamine; |

| No. | Structure | Name |
|---|---|---|
| 28 | 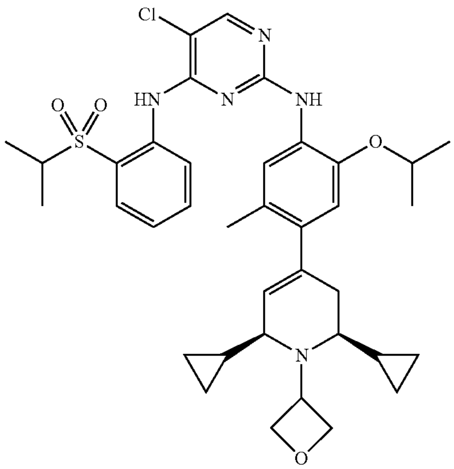 [SMILES: Cc1cc(Nc2ncc(Cl)c(Nc3ccccc3S(=O)(=O)C(C)C)n2)c(OC(C)C)cc1C1=C[C@H](C2CC2)N(C2COC2)[C@H](C2CC2)C1] | 5-chloro-N²-(4-((cis)-2,6-dicyclopropyl-1-(oxetan-3-yl)-1,2,3,6-tetrahydropyridin-4-yl)-2-isopropoxy-5-methylphenyl)-N⁴-(2-(isopropylsulfonyl)phenyl)pyrimidine-2,4-diamine; |
| 29 | 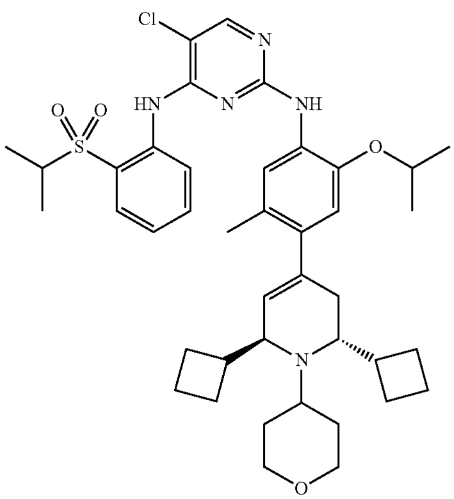 [SMILES: Cc1cc(Nc2ncc(Cl)c(Nc3ccccc3S(=O)(=O)C(C)C)n2)c(OC(C)C)cc1C1=C[C@H](C2CCC2)N(C2CCOCC2)[C@@H](C2CCC2)C1] | 5-chloro-N²-(4-((trans)-2,6-dicyclobutyl-1-(tetrahydro-2H-pyran-4-yl)-1,2,3,6-tetrahydropyridin-4-yl)-2-isopropoxy-5-methylphenyl)-N⁴-(2-(isopropylsulfonyl)phenyl)pyrimidine-2,4-diamine; |
| 30 | 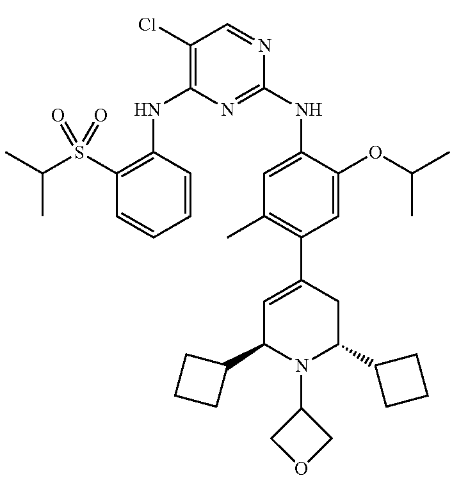 [SMILES: Cc1cc(Nc2ncc(Cl)c(Nc3ccccc3S(=O)(=O)C(C)C)n2)c(OC(C)C)cc1C1=C[C@H](C2CCC2)N(C2COC2)[C@@H](C2CCC2)C1] | 5-chloro-N²-(4-((trans)-2,6-dicyclobutyl-1-(oxetan-3-yl)-1,2,3,6-tetrahydropyridin-4-yl)-2-isopropoxy-5-methylphenyl)-N⁴-(2-(isopropylsulfonyl)phenyl)pyrimidine-2,4-diamine; |

| No. | Structure | Name |
|---|---|---|
| 31 | 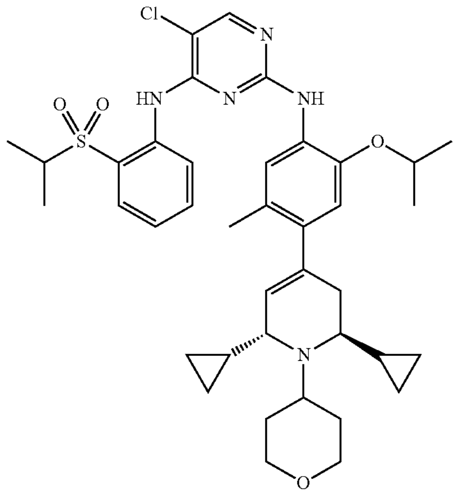 [SMILES: Cc1cc(Nc2ncc(Cl)c(Nc3ccccc3S(=O)(=O)C(C)C)n2)c(OC(C)C)cc1C1=C[C@@H](C2CC2)N(C2CCOCC2)[C@H](C2CC2)C1] | 5-chloro-$N^2$-(4-((trans)-2,6-dicyclopropyl-1-(tetrahydro-2H-pyran-4-yl)-1,2,3,6-tetrahydropyridin-4-yl)-2-isopropoxy-5-methylphenyl)-$N^4$-(2-(isopropylsulfonyl)phenyl)pyrimidine-2,4-diamine; or |
| 32 | | 5-chloro-$N^2$-(4-((trans)-2,6-dicyclopropyl-1-(oxetan-3-yl)-1,2,3,6-tetrahydropyridin-4-yl)-2-isopropoxy-5-methylphenyl)-$N^4$-(2-(isopropylsulfonyl)phenyl)pyrimidine-2,4-diamine | or a pharmaceutically acceptable salt or solvate thereof.

8. The method according to claim 1, wherein the ALK inhibitor is 5-chloro-$N^2$-(2-isopropoxy-5-methyl-4-(tetrahydro-2H-pyran-4-yl)-1,2,3,6-tetrahydropyridin-4-yl)phenyl)-$N^4$-(2-(isopropylsulfonyl)phenyl)pyrimidine-2,4-diamine, or a pharmaceutically acceptable salt or solvate thereof.

9. The method according to claim 1, wherein the EGFR inhibitor, or a pharmaceutically acceptable salt or solvate thereof, is selected from the group consisting of icotinib, osimertinib (AZD9291), afatinib, Avitinib, gefitinib, erlotinib, lapatinibxylenesulphonate, neratinib, cetuximab, pamumab, vannameib, nexizumab, AG-490, tyrosine phosphorylation inhibitor AG 1478, CL-387 CL-785, oncogene inhibitor analog, PD 168393, PKC-412, PD 174265, tyrosine phosphorylation inhibitor 51, butein, valanib dihydrochloride, tyrosine phosphorylation inhibitor 47, AG 494, tyrosine phosphorylation inhibitor AG 112, AZD8931, CUDC-101, XL647, AG 43, (+)shy-Aeroplysinin-L PD 153035, OSI-420 free base (demethyl erlotinib), WZ4002, tyrosine phosphorylation inhibitor B44, (−)enantiomer, tyrosine phosphorylation inhibitor B44, (+)enantiomer, PD161570, neratinib, HDS029, erlotinib-d6, lavendustin C methyl ester, RO 106-9920, tyrosine phosphorylation inhibitor AG 99, AG 555, AG 556, RG-13022, tyrosine phosphorylation inhibitor RG 14620, DAPH, BPIQ-II HCl salt, didesmethyl erlotinib hydrochloride, demethyl erlotinib acetate, PD 153035 hydrochloride, BIBS 1382, GW2974, PD 166285, pilitinib, EGFR inhibitor III, AST 1306, gefitinib hydrochloride, ARRY334543, dacomitinib, getitinib O-methyl-D3, OSI-420-d4, free base (demethyl erlotinib-d4), LFM-Al2, BPDQ, tyrosine phosphorylation inhibitor 47, tyrosine phosphorylation inhibitor AG 528, BPIQ-I, getitinib dihydrochloride, carnitinib dihydrochloride, GW 583340 dihydrochloride, BIBU 1361 dihydrochloride, TAK 285, WZ 3146, WZ8040, O-demethyl gefitinib, O-demorpholinopropyl gefitinib, TAK 165, and CGP 74514A.

10. The method according to claim 1, wherein the cancer is non-small cell lung cancer.

11. The method according to claim 1, wherein the ALK inhibitor, or a pharmaceutically acceptable salt or solvate thereof, is administrated in an amount of from about 0.005 mg/day to about 5000 mg/day.

12. The method according to claim 1, wherein the ALK inhibitor, or a pharmaceutically acceptable salt or solvate thereof, is administrated in an amount of from about 1 mg/kg to about 200 mg/kg.

13. The method according to claim 1, wherein the EGFR inhibitor, or a pharmaceutically acceptable salt or hydrate thereof, is administrated in an amount of from 0.005 mg/day to about 5000 mg/day.

14. The method according to claim 1, wherein the EGFR inhibitor, or a pharmaceutically acceptable salt or solvate thereof, is administrated in an amount of from about 1 mg/kg to about 200 mg/kg.

15. A pharmaceutical composition, comprising an ALK inhibitor, or a pharmaceutically acceptable salt or solvate thereof, and an EGFR inhibitor, or a pharmaceutically acceptable salt or solvate thereof, and a pharmaceutically acceptable carrier, wherein:
(i) the ALK inhibitor is a compound of Formula I:
wherein:
$R^{1a}$ and $R^{1b}$ are independently selected from the group consisting of hydrogen, $C_{1-6}$ alkyl, and $C_{3-8}$ cycloalkyl;
$R^{2a}$ and $R^{2b}$ are independently selected from the group consisting of hydrogen, $C_{1-6}$ alkyl, and $C_{3-8}$ cycloalkyl;
$R^3$ is selected from the group consisting of hydrogen, $C_{1-6}$ alkyl, $C_{3-6}$ cycloalkyl, and 4- to 8-membered heterocyclyl,
$R^4$ is selected from the group consisting of $C_{1-4}$ alkyl and $C_{3-6}$ cycloalkyl;
$R^5$ is halo;
$R^6$ is selected from the group consisting of $C_{1-4}$ alkyl and $C_{3-6}$ cycloalkyl; and
$R^7$ is selected from the group consisting of hydrogen, $C_{1-4}$ alkyl, and $C_{3-6}$ cycloalkyl,
with proviso that when $R^{1a}$, $R^{1b}$, $R^{2a}$, and $R^{2b}$ are each hydrogen, then $R^3$ is selected from the group consisting of $C_{3-6}$ cycloalkyl and 4- to 8-membered heterocyclyl; and
(ii) the EGFR inhibitor is selected from the group consisting of icotinib, osimertinib (AZD9291), afatinib, Avitinib, gefitinib erlotinib, lapatinibxylenesulphonate, neratinib, cetuximab, pamumab, vannameib, nexizumab, AG-490, tyrosine phosphorylation inhibitor AG 1478 CL-785, oncogene inhibitor analog, PD 168393, PKC-412, PD 174265, tyrosine phosphorylation inhibitor 51, butein, valanib dihydrochloride, tyrosine phosphorylation inhibitor 47, AG 494, tyrosine phosphorylation inhibitor AG 112, AZD8931, CUDC-101, XL647, AG 43, (+)shy-Aeroplysinin-1, PD 153035, OSI-420 free base (demethyl erlotinib), WZ4002, tyrosine phosphorylation inhibitor B44, (−)enantiomer, tyrosine phosphorylation inhibitor B44, (+)enantiomer, PD161570, neratinib, HDS029, erlotinib-d6, lavendustin C methyl ester, RO 106-9920, tyrosine phosphorylation inhibitor AG 99, AG 555, AG 556, RG-13022, tyrosine phosphorylation inhibitor RG 14620, DAPH, BPIQ-II HCl salt, didesmethyl erlotinib hydrochloride, demethyl erlotinib acetate, PD 153035 hydrochloride, BIBX 1382, GW2974, PD 166285, pilitinib, EGFR inhibitor III, AST 1306, gefitinib hydrochloride, ARRY334543, dacomitinib, gefitinib O-methyl-D3, OSI-420-d4, free base (demethyl erlotinib-d4), LFM-A12, BPDQ, tyrosine phosphorylation inhibitor 47, tyrosine phosphorylation inhibitor AG 528, BPIQ-I, gefitinib dihydrochloride, carnitinib dihydrochloride, GW 583340 dihydrochloride, BIBU 1361 dihydrochloride, TAK 285, WZ 3146, WZ8040, O-demethyl gefitinib, O-demorpholinopropyl gefitinib, TAK 165, and CGP 74514A.

16. A kit, comprising:
(a) a first component in a first container, the first component comprising an ALK inhibitor, or a pharmaceutically acceptable salt or solvate thereof, and optionally a pharmaceutically acceptable carrier;
(b) a second component in a second container, the second component comprising an EGFR inhibitor, or a pharmaceutically acceptable salt or solvate thereof, and optionally a pharmaceutically acceptable carrier; and
(c) an optional specification, wherein:
(i) the ALK inhibitor is a compound of Formula I:

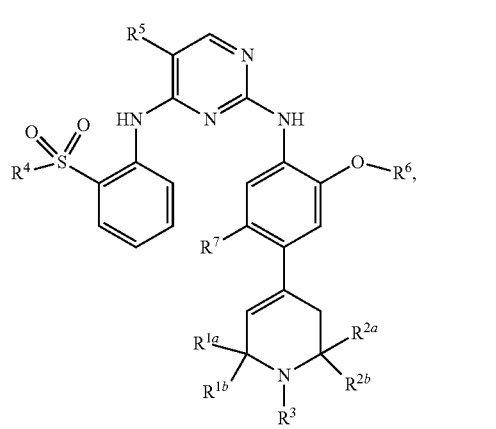

wherein:
$R^{1a}$ and $R^{1b}$ are independently selected from the group consisting of hydrogen, $C_{1-6}$ alkyl, and $C_{3-8}$ cycloalkyl;
$R^{2a}$ and $R^{2b}$ are independently selected from the group consisting of hydrogen, $C_{1-6}$ alkyl, and $C_{3-8}$ cycloalkyl;
$R^3$ is selected from the group consisting of hydrogen, $C_{1-6}$ alkyl, $C_{3-6}$ cycloalkyl, and 4- to 8-membered heterocyclyl,
$R^4$ is selected from the group consisting of $C_{1-4}$ alkyl and $C_{3-6}$ cycloalkyl;
$R^5$ is halo;
$R^6$ is selected from the group consisting of $C_{1-4}$ alkyl and $C_{3-6}$ cycloalkyl; and
$R^7$ is selected from the group consisting of hydrogen, $C_{1-4}$ alkyl, and $C_{3-6}$ cycloalkyl,
with proviso that when $R^{1a}$, $R^{1b}$, $R^{2a}$, and $R^{2b}$ are each hydrogen, then $R^3$ is selected from the group consisting of $C_{3-6}$ cycloalkyl and 4- to 8-membered heterocyclyl; and
(ii) the EGFR inhibitor is selected from the group consisting of icotinib, osimertinib (AZD9291), afatinib Avitinib, gefitinib, erlotinib, lapatinibxylenesulphonate, neratinib, cetuximab, pamumab, vannameib, nexizumab, AG-490, tyrosine phosphorylation inhibitor AG 1478, CL-387, CL-785, oncogene inhibitor analog, PD 168393, PKC-412, PD 174265, tyrosine phosphorylation inhibitor 51, butein, valanib dihydrochloride, tyrosine phosphorylation inhibitor 47, AG 494, tyrosine phosphorylation inhibitor AG 112, AZD8931, CUDC-101, XL647, AG 43, (+)shy-Aeroplysinin-1, PD 153035, OSI-420 free base (demethyl erlotinib), WZ4002 tyrosine phosphorylation inhibitor B44, (−)enantiomer, tyrosine phosphorylation inhibitor B44, (+)enantiomer, PD161570, neratinib, HDS029, erlotinib-d6, lavendustin C methyl ester, RO 106-9920, tyrosine phosphorylation inhibitor AG 99, AG 555, AG 556, RG-13022, tyrosine phosphorylation inhibitor RG 14620, DAPH, BPIQ-II HCl salt, didesmethyl erlotinib hydrochloride, demethyl erlotinib acetate, PD 153035 hydrochloride, BIBX 1382, GW2974, PD 166285, pilitinib, EGFR inhibitor III, AST 1306, gefitinib hydrochloride, ARRY334543, dacomitinib, gefitinib O-methyl-D3, OSI-420-d4, free base (demethyl erlotinib-d4), LFM-A12, BPDQ, tyrosine phosphorylation inhibitor 47, tyrosine phosphorylation inhibitor AG 528, BPIQ-I, gefitinib dihydrochloride, carnitinib dihydrochloride, GW 583340 dihydrochloride, BIBU 1361 dihydrochloride, TAK 285, WZ 3146, WZ8040, O-demethyl gefitinib, O-demorpholinopropyl gefitinib, TAK 165, and CGP 74514A.

17. The method according to claim 1, wherein the EGFR inhibitor, or a pharmaceutically acceptable salt or solvate thereof, is selected from the group consisting of osimertinib (AZD9291), afatinib and avitinib.

18. The method according to claim 1, wherein the cancer is non-small cell lung cancer carrying an $EGFR^{T790M}$ mutation.

* * * * *

UNITED STATES PATENT AND TRADEMARK OFFICE
CERTIFICATE OF CORRECTION

PATENT NO. : 11,478,477 B2
APPLICATION NO. : 16/627046
DATED : October 25, 2022
INVENTOR(S) : Dajun Yang et al.

Page 1 of 1

It is certified that error appears in the above-identified patent and that said Letters Patent is hereby corrected as shown below:

In the Claims

In Claim 1, at Column 45, Lines 43-44, replace "breast cancer cervical cancer" with -- breast cancer, cervical cancer --.

In Claim 1, at Column 46, Line 27, delete "wherein:" and at Line 47, insert -- wherein: --.

In Claim 2, at Column 47, Line 3, delete "wherein:" and at Line 26, insert -- wherein: --.

In Claim 7, at Column 62, in the name of structure No. 24, replace "isoproxy" with -- isopropoxy --.

In Claim 9, at Column 67, Lines 62-63, replace "(+)shy-Aeroplysinin-L PD 153035" with -- (+)shy-Aeroplysinin-L, PD 153035 --.

In Claim 9, at Column 68, Line 47, replace "BIBS 1382" with -- BIBX 1382 --.

In Claim 9, at Column 68, Lines 49-50, replace "getitinib O-methyl-D3" with -- gefitinib O-methyl-D3 --.

In Claim 9, at Column 68, Line 53, replace "getitinib dihydrochloride" with -- gefitinib dihydrochloride --.

In Claim 15, at Column 69, Lines 38-39, replace "inhibitor AG 1478 CL-785" with -- inhibitor AG 1478, CL-387, CL-785 --.

In Claim 15, at Column 69, Line 58, delete "tyrosine phosphorylation inhibitor 47".

In Claim 16, at Column 70, Line 60, replace "WZ4002 tyrosine" with -- WZ4002, tyrosine --.

In Claim 16, at Column 71, Lines 5-6, delete "tyrosine phosphorylation inhibitor 47".

Signed and Sealed this
Twenty-fourth Day of December, 2024

Derrick Brent
*Acting Director of the United States Patent and Trademark Office*